US007842476B2

(12) United States Patent
McGregor et al.

(10) Patent No.: US 7,842,476 B2
(45) Date of Patent: Nov. 30, 2010

(54) IN VITRO PEPTIDE EXPRESSION LIBRARY

(75) Inventors: Duncan McGregor, Cambridge (GB);
Richard Odegrip, Stockholm (SE);
Kevin Fizgerald, Essex (GB);
Rosemarie Hederer, Cambridge (GB);
Bill Eldridge, Essex (GB); Chris Ullman, Cambridge (GB); Philip Kuhlman, Cambridgeshire (GB); David Coomber, New South Wales (AU)

(73) Assignee: Isogenica Limited, Peterborough (GB)

( * ) Notice: Subject to any disclaimer, the term of this patent is extended or adjusted under 35 U.S.C. 154(b) by 538 days.

(21) Appl. No.: 10/526,479

(22) PCT Filed: Sep. 5, 2003

(86) PCT No.: PCT/GB03/03860

§ 371 (c)(1),
(2), (4) Date: Apr. 8, 2005

(87) PCT Pub. No.: WO2004/022746

PCT Pub. Date: Mar. 18, 2004

(65) Prior Publication Data

US 2006/0035232 A1 Feb. 16, 2006

(30) Foreign Application Priority Data

| Sep. 6, 2002 | (GB) | ................................. 0220759.5 |
| Feb. 27, 2003 | (GB) | ................................. 0304521.8 |
| Feb. 28, 2003 | (GB) | ................................. 0304657.0 |

(51) Int. Cl.
*C12P 21/06* (2006.01)
*C12P 19/34* (2006.01)
*C12Q 1/68* (2006.01)
*C12N 15/00* (2006.01)

(52) U.S. Cl. .......................... 435/69.1; 435/6; 435/91.1; 435/320.1

(58) Field of Classification Search .................. None
See application file for complete search history.

(56) References Cited

U.S. PATENT DOCUMENTS 5,716,780 A * 2/1998 Edwards et al. ................. 435/6

FOREIGN PATENT DOCUMENTS

| EP | 1 350 845 | 10/2003 |
| EP | 1 350 846 | 10/2003 |
| WO | WO 91/05058 | 4/1991 |
| WO | 96/40987 | 12/1996 |
| WO | 98/37186 | 8/1998 |
| WO | 98/54312 | 12/1998 |
| WO | WO 99/02671 | 1/1999 |
| WO | 99/11785 | 3/1999 |
| WO | WO 00/40712 | 7/2000 |
| WO | WO 00/60070 | 10/2000 |
| WO | 03/014734 | 2/2003 |

OTHER PUBLICATIONS

Doi et al. FEBS Letters, vol. 457, pp. 227-230 (1999).*
Int'l Search Report for related Int'l Appln. No. PCT/GB03/03860 dated Jan. 9, 2004.
GB Search Report for related Appln. No. 0220759.5 dated Feb. 23, 2003.
M.G. Cull et al. "Screening for receptor ligands using large libraries of peptides linked to the C terminus of the *lac* repressor" Proceedings of the National Academy of Sciences U.S.A., Mar. 1, 1992, vol. 89, No. 5, pp. 1865-1869.
J. Praszkier et al. "Role of *CIS* in replication of an IncB plasmid" Journal of Bacteriology, May 1999, vol. 181, No. 9, pp. 1765-2772.
D.P. McGregor et al. "External surface display of proteins linked to DNA-binding domains" Analytical Biochemistry, Jul. 15, 2001, vol. 294, No. 2, pp. 108-117.
Barrett et al. "Selective enrichment and characterization of high affinity ligands from collections of random peptides on filamentous phage" Anal. Biochem. 204:357-364 (1992).
Derbyshire et al. "*Cis* preference of the *IS903* transposase is mediated by combination of transposase instability and inefficient translation" Mol. Microbiol. 21:1261-1272 (1996).
Hanes et al. "In vitro selection and evolution of functional proteins by using ribosome display" Proc. Natl. Acad. Sci. USA 94:4937-4942 (1997).
Giraldo et al. "Differential bidning of wild-type and a mutant RepA prtoein to *oriR* sequence suggests a model for the initiation of plasmid R1 replication" J. Mol. Biol. 228:787-802 (1992).
Mader et al. "Defining a minimal estrogen receptor DNA binding domain" Nucl. Acids Res. 21:1125-1132 (1993).
McFall et al. "*Cis*-acting proteins" J. Bacteriol. 167:429-432 (1986).
Marks et al. "By-passing immunization: Human antibodies from V-gene libraries displayed on phage" J. Mol. Biol. 222:581-597 (1991).
Masai et al. "Definition of *oriR*, the minimum DNA segment essential for initiation of R1 plasmid replication in vitro" Proc. Natl. Acad. Sci. USA 80:6814-6818 (1983).
Masai et al. "*RepA* protein- and *oriR*-dependent initiation of R1 plasmid replication: Identification of a *rho*-dependent transcription terminator required for *cis*-action of *repA* protein" Nucl. Acids Res. 16:6493-6514 (1988).
Mattheakis et al. "An in vitro polysome display system for identifying ligands from very large peptide libraries" Proc. Natl. Acad. Sci. USA 91:9022-9026 (1994).
Murdoch et al. "Estrogen receptor binding to a DNA response element in vitro is not dependent upon estradiol" Biochem. 29:8377-8385 (1990).

(Continued)

*Primary Examiner*—Janet L. Epps-Smith
(74) *Attorney, Agent, or Firm*—Nixon & Vanderhye P.C.

(57) ABSTRACT

The invention provides a method for making in vitro peptide expression libraries, and for the isolation of nucleotide sequences encoding peptides of interest, wherein the peptides or proteins are specifically associated with the DNA encoding them through non-covalent protein:DNA binding. The method describes ways of making the library itself, DNA molecules encoding the library and uses of the expression library.

34 Claims, 7 Drawing Sheets

OTHER PUBLICATIONS

Nikoletti et al. "Analysis of the incompatibility determinants of I-complex plasmids" J. Bacteriol. 170:1311-1318 (1988).

Parmley et al. "Antibody-selectable filamentous fd phage vectors: Affinity purification of target genes" Gene 73:305-318 (1988).

Praszkier et al. "Comparative analysis of the replication regions of IncB, IncK, and IncZ plasmids" J. Bacteriol. 173:2393-2397 (1991).

Praszkier et al. "Effect of CIS on activity in trans of the replication initiator protein of an IncB plasmid" J. Bacteriol. 182:3972-3980 (2000).

Smith "Filamentous fusion phage: Novel expression vectors that display cloned antigens on the virion surface" Science 228:1315-1317 (1985).

Williamson et al. "Human monoclonal antibodies against a plethora of viral pathogens from single combinatorial libraries" Proc. Natl. Acad. Sci. USA 90:4141-4145 (1993).

Zubay "In vitro synthesis of protein in microbial systems" Ann. Rev. Genet. 7:267-287 (1973).

Doi et al., "Stable: Protein-DNA Fusion System for Screening of Combinatorial Protein Libraries in Vitro", *FEBS Letters*, 457:227-230 (1999).

Echols, et al., "On the Nature of Cis-Acting Regulatory Proteins and Genetic Organization in Bacteriophage: The Example of Gene Q of Bacteriophage λ", *Genetics*, 83:5-10 (1976).

Bertschinger et al., "Selection of Single Domain Binding Proteins by Covalent DNA Display", *Engineering, Design and Selection*, 20:57-68 (2007).

Tawfik and Griffiths, "Man-made Cell-like Compartments for Molecular Evolution", *Nature Biotechnology*, 16:652-656 (1998).

Yonezawa et al., "DNA Display for in Vitro Selection of Diverse Peptide Libraries", *Nucleic Acids Research*, 31(19 el 18):1-5 (2003).

\* cited by examiner

IN VITRO PEPTIDE EXPRESSION LIBRARY

This application is a US national phase of Int'l Appln. No. PCT/GB2003/003860, filed 6 Sep. 2002, which designated the U.S. and claims priority of Appln. Nos. GB 0220759.5, filed 6 Sep. 2002, GB 0304521.8, filed 27 Feb. 2003, and GB 0304657.0, filed 28 Feb. 2003, the entire content of each of which are hereby incorporated by reference.

FIELD OF THE INVENTION

The present invention relates generally to recombinant DNA technology and, more particularly, to in vitro methods for constructing and screening DNA libraries for DNA sequences that encode biologically active molecules.

BACKGROUND OF THE INVENTION

Isolating an unknown gene which encodes a desired peptide from a recombinant DNA library can be a difficult task. The use of hybridisation probes may facilitate the process, but their use is generally dependent on knowing at least a portion of the sequence of the gene which encodes the protein. When the sequence is not known, DNA libraries can be expressed in an expression vector, and antibodies have been used to screen plaques or colonies for the desired protein antigen. This procedure has been useful in screening small libraries, but rarely occurring sequences which are represented in less than about 1 in $10^5$ clones, as is the case with rarely occurring cDNA molecules or synthetic peptides, can be easily missed, making screening libraries larger than $10^6$ clones at best laborious and difficult. Screening larger libraries has required the development of methods designed to address the isolation of rarely occurring sequences, which are based on the co-selection of molecules, along with the DNAs that encode them. In vivo methods have been developed to screen large libraries, such as phage display and "peptides on plasmids" using lacI fusions of peptides.

Phage display is based on DNA libraries fused to the N-terminal end of filamentous bacteriophage coat proteins and their expression in a bacterial host resulting in the display of foreign peptides on the surface of the phage particle with the DNA encoding the fusion protein packaged in the phage particle (Smith G. P., 1985, Science 228: 1315-1317). Libraries of fusion proteins incorporated into phage, can then be selected for binding members against targets of interest (ligands). Bound phage can then be allowed to reinfect *Escherichia coli* (*E. coli*) bacteria and then amplified and the selection repeated, resulting in the enrichment of binding members (Parmley, S. F., & Smith, G. P. 1988., Gene 73: 305-318; Barrett R. W. et al., 1992, Analytical Biochemistry 204: 357-364 Williamson et al., Proc. Natl. Acad. Sci. USA, 90: 4141-4145; Marks et al., 1991, J. Mol. Biol. 222: 581-597).

LacI fusion plasmid display is based on the DNA binding ability of the lac repressor. Libraries of random peptides are fused to the C-terminal end of the lacI repressor protein. Linkage of the LacI-peptide fusion to its encoding DNA occurs via the lacO sequences on the plasmid, forming a stable peptide-LacI-peptide complex. These complexes are released from their host bacteria by cell lysis, and peptides of interest isolated by affinity purification on an immobilised receptor target. The plasmids thus isolated can then be reintroduced into *E. coli* by electroporation to amplify the selected population for additional rounds of screening (Cull, M. G. et al. 1992. Proc. Natl. Acad. Sci. U.S.A. 89:1865-1869).

These bacterial methods are limited by the size of the library that can be created by current methods of introducing DNA into host bacteria, the potential cellular toxicity, of the expressed peptides introduced, and by the inability to introduce post-translational modifications, or to incorporate novel amino acids into the expressed peptide.

An entirely in vitro ribosome system has been described based on the linkage of peptides to the RNA encoding them through the ribosome (WO91/05058). Ribosome display has also been used for the selection of single-chain Fv antibody fragments (scFv) (Matheakis, L. C. et al., 1994 Proc. Natl. Acad. Sci. USA, 91: 9022-9026; Hanes, J. & Pluckthun, A. 1997 Proc. Natl. Acad. Sci. USA, 94: 4937-4942). This method suffers from the lower stability of the RNA genetic material and the increased degradation likely under certain selection conditions where RNAse is likely to be present.

The in vitro method described by Griffiths and Tawfik (WO 99/02671 and WO 00/40712) addresses some of these concerns by compartmentalizing DNA prior to expression of peptides, which then modify the DNA within the compartment. Peptides capable of modifications, resulting from enzymatic activity of interest, are then selected in a subsequent step. However, no direct selection of peptide binding activity is possible of both peptide and DNA without modification of the DNA encoding that peptide, and by releasing the modified DNA from the compartment.

Another prior art method, covalent display technology, or CDT, is described in WO9837186. This method relies on covalent linkage of protein to DNA to retain the linkage of genotype to phenotype, through the cis action of the crosslinking protein. This method teaches that two requirements are needed for successful use of this technique. Firstly, proteins are required which interact in vitro with the DNA sequence which encodes them (cis action), and secondly, said proteins must establish a covalent linkage to their own DNA template. This method suffers from the fact that the DNA is chemically modified which can prevent the recovery and identification of the binding peptide of interest.

There remains a need for more versatile in vitro methods of constructing peptide libraries in addition to the methods described above, which can allow direct selection of binding activity, as well as for enzymatic activity, and that allow efficient production of complex peptide structures, while still allowing recovery of intact genetic material encoding the peptide of interest.

SUMMARY OF THE INVENTION

The present invention therefore provides a method for producing an in vitro peptide expression library comprising a plurality of peptides, wherein each peptide is linked to a DNA construct encoding the peptide, comprising the steps of:
  (a) providing a DNA construct comprising:
    (i) a DNA target sequence;
    (ii) DNA encoding a library member peptide; and
    (iii) DNA encoding a peptide capable of non-covalently binding directly or indirectly to said DNA target sequence of (ii);
    wherein said DNA construct and encoded protein are selected to have cis-activity;
  (b) expressing a plurality of DNA constructs according to (a), wherein said DNA constructs encode a plurality of library member peptides such that each expressed peptide is non-covalently linked to the DNA from which it was produced.

Also provided is a method for producing an in vitro peptide expression library comprising a plurality of peptides, wherein each peptide is linked to the DNA construct encoding the peptide, comprising the steps of:

(a) providing a DNA construct comprising:
  (i) DNA encoding a library member peptide; and
  (ii) DNA encoding a peptide capable of non-covalently binding to a bifunctional agent:
  wherein said DNA construct and encoded protein are selected to have cis-activity;
(b) binding a bifunctional agent or a DNA tag capable of binding a bifunctional agent to said DNA construct of (a), wherein said bifunctional agent is capable of binding to the peptide encoded by said DNA of (ii); and
(c) expressing a plurality of DNA construct according to (b), wherein said DNA constructs encode a plurality of library member peptides such that each expressed peptide is linked via said bifunctional agent to the DNA from which it was produced.

The present invention extends to the peptide libraries produced by such methods and to the DNA constructs used in such methods.

The present invention also provides methods of screening in vitro peptide expression libraries of the invention. In one aspect there is provided a method of identifying and/or purifying a peptide exhibiting desired properties from an in vitro peptide expression library produced according to the method of any one of the preceding claims, comprising at least the steps of (a) screening said library and (b) selecting and isolating the relevant library member. In a second aspect, there is provided a method of identifying a specific ligand binding peptide, said method comprising at least the steps of (a) screening an in vitro peptide expression library produced according to the method of the invention with ligand molecules which are optionally bound to a solid support; (b) selecting and isolating a library member binding to said target molecule; and (c) isolating the peptide which binds specifically to said target molecule. In a third aspect there is provided a method of identifying and/or purifying a peptide having the ability to bind a specific DNA target sequence comprising at least the steps of (a) providing an in vitro expression library according to the invention wherein said peptide or protein of (iii) is a library member peptide having DNA binding activity and wherein said DNA target sequence of (i) is the target sequence of interest (b) selecting and isolating a library member in which the encoded protein binds to said target sequence; (c) isolating the peptide which binds to said target sequence.

In addition to isolating and/or identifying specific peptides from the libraries of the invention, the screening methods of the invention may be used to isolate and/or identify the DNA encoding specific peptides from the library.

BRIEF DESCRIPTION OF THE SEQUENCES

Figure 1:
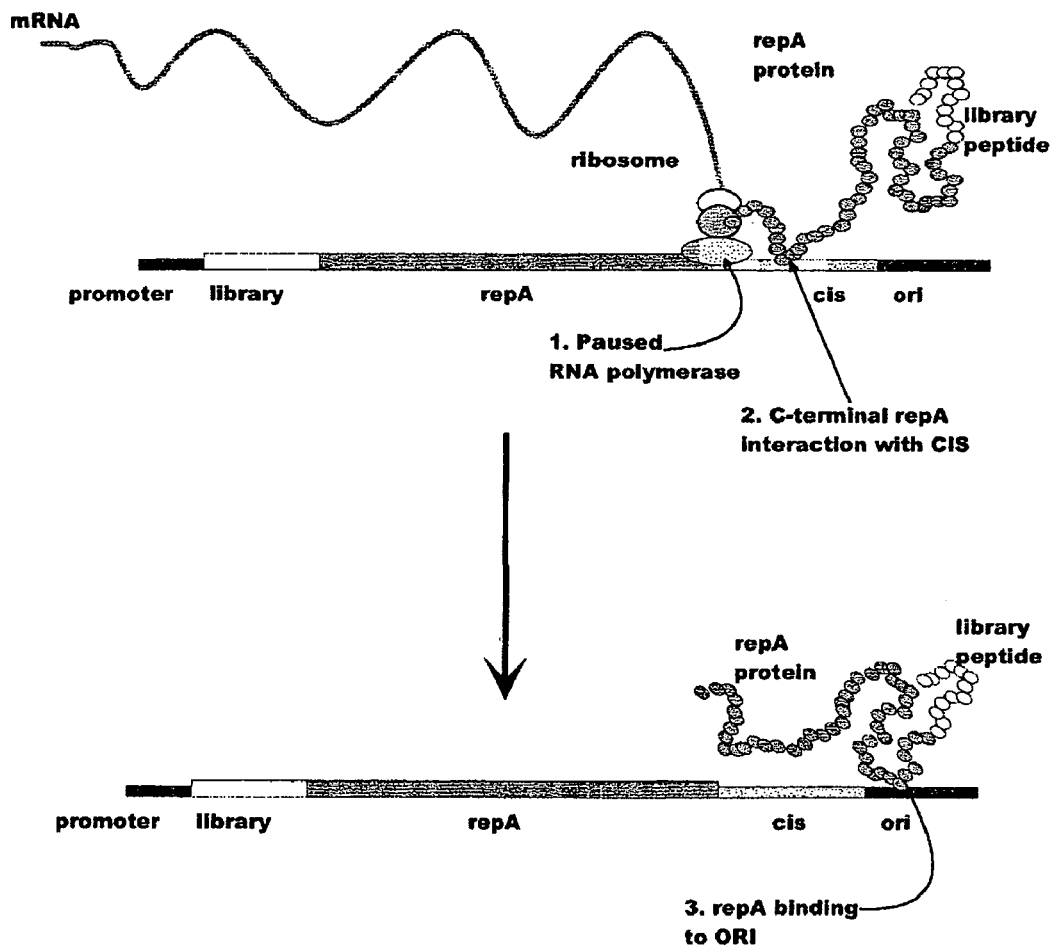
FIG. 1 gives a schematic representation of a method by which a DNA construct of the invention may be linked to the peptide that it encodes.

SEQ ID Nos 1 to 11, 19 to 23, 26 to 35 and 45 to 47 show the primers used in the Examples.

SEQ ID NO: 12 shows the sequence of the TAC-MYC-CK-REPA-CIS-ORI construct. SEQ ID NO: 13 shows the sequence of the TAC-MYC-V5-REPA-CIS-ORI construct. SEQ ID NO: 24 shows the sequence of the TAC-V5-REPA-CIS-ORI-408 construct and SEQ ID NO: 25 shows the sequence of the TAC-NNB-REPA-CIS-ORI-408 construct.

SEQ ID NO: 14 shows the estrogen receptor target recognition sequence.

SEQ ID Nos 15 and 16 show the DNA and amino acid sequences of the repA gene from the R1 plasmid of the incFII incompatibility group. SEQ ID Nos 17 and 18 show the sequences of the CIS DNA element and ori sequence form the same system.

SEQ ID Nos 36 to 39 show the sequences of peptides isolated after selection in Example 5. SEQ ID Nos 39 to 43 show the sequences of clones isolated in Example 6.

DETAILED DESCRIPTION OF THE INVENTION

The present invention relates to the construction and screening of a library for a nucleotide sequence which encodes a peptide of interest in vitro. The constructs encoding the peptide of interest are designed such that the expressed peptide shows cis activity for the construct. Cis activity is defined as the ability of the peptide to bind to the DNA from which the peptide was produced, i.e. from which it was transcribed and translated. In vitro expression of the construct results in binding of the peptide to the DNA encoding that same peptide molecule by non-covalent interaction. This differs from the teaching of WO 98/37186, which does not allow for the possibility of in vitro non-covalent interaction between protein and the DNA it encodes, and indeed specifically excludes such interactions from having any practical use for library screening.

Non-covalent binding refers to an association that may be disrupted by methods well known to those skilled in the art, such as the addition of an appropriate solvent, or a change in ionic conditions, for example, the addition of low pH glycine or high pH triethylamine. In the present case, a typical example of non-covalent binding would be the non-covalent interaction between a DNA binding protein and a DNA molecule. Conversely, when a covalent linkage is formed between the DNA and the encoded polypeptide, the displayed peptide or protein will not be released from the DNA by ionic conditions and solvents that would disrupt non-covalent DNA binding protein:DNA interactions. For example, the bacterial replication protein repA binds non-covalently to its target DNA sequence oriR and can be released from this target DNA sequence at salt concentrations greater than 0.2M KCl (Giraldo R. & Diaz R. 1992 J. Mol. Biol. 228: 787-802). This salt concentration would not affect a covalent linkage, which would require much harsher conditions to release the covalently bound protein, with the increased risk of damage to the recovered DNA.

The current invention describes cis activity and non-covalent binding which allow the encoded peptide or protein to remain associated with the DNA construct with a half life sufficient to allow individual peptides and the associated DNA encoding that peptide with an activity of interest to be separated from the resulting mixture of protein DNA complexes. For example, the association between the encoded protein and its DNA may have a half life of up to 30 minutes, up to 45 minutes up to one hour, up to 2 hours, up to 6 hours or up to 12 hours. The screening methods of the invention may therefore be carried out immediately, after construction of the library, or later, for example up to one, up to two, up to six, up to twelve hours or up to twenty four hours or more than twenty four hours later.

Surprisingly, therefore, the invention described herein demonstrates that such encoded peptides or proteins can be expressed in vitro and bound to the DNA encoding that peptide in the presence of other DNA sequences. The invention also demonstrates that covalent linkage between protein and DNA is not required to maintain such cis activity, and that a non-covalent interaction between DNA and binding protein is sufficient to allow selection of peptides in an in vitro expression and selection system.

According to the present invention, individual DNA library members, each of which encodes a peptide to be expressed in the peptide expression library (library member peptide), are placed in a suitable DNA construct. The DNA construct into which the DNA library member is placed includes all the sequences necessary to allow expression of the library member peptide from the construct and to allow the peptide encoded by the construct to bind to the DNA construct which encoded it. Each peptide in the library will typically comprise a fusion protein comprising the library member peptide fused to a peptide involved in bindings of the fusion protein to the relevant DNA construct. Such fusion proteins may comprise further sequences and said library peptide may be joined to said binding peptide via a linker sequence.

A plurality of such constructs, encoding a plurality of different library member peptides form a DNA library of the invention. Expressing such a library of DNA molecules results in the non-covalent binding of individual encoded proteins to the DNA which encoded them and from which they have been transcribed and translated, in the presence of many other DNA molecules that encode other members of the library. The sequence encoding the peptide library member present in a particular encoded protein will therefore be present in the DNA which is bound to that protein. This process therefore links the library member peptide, in a biologically active form (usually having a binding activity) to the specific library member DNA sequence encoding that peptide, allowing selection of peptides of interest, for example due to a particular binding activity, and subsequent isolation and identification of the DNA encoding that library member peptide.

For the purposes of the invention a DNA library is therefore a population of DNA constructs. Each construct comprises a DNA sequence encoding a peptide to be expressed as a library member peptide and each contains appropriate promoter, translation start and stop signals. A DNA library of the invention will contain a plurality of such DNA molecules. A plurality of DNA constructs are provided each encoding a library member peptide to provide a plurality of different library members. Preferably a DNA library will contain at least $10^4$ discrete DNA molecules. For example, a DNA library may contain more than $10^6$, more than $10^8$, more than $10^{10}$, more than $10^{12}$ or more than $10^{14}$ discrete DNA molecules.

A peptide expression library is defined as a population of peptide sequences expressed from a library of DNA molecules. A peptide expression library of the present invention therefore encompasses a library of peptides which are non-covalently bound to the DNA which encoded them. For example, a peptide expression library of the present invention malt be a library of at least $10^4$ discrete proteins each comprising a library peptide sequence, expressed from a library of DNA molecules. A peptide expression library of the invention may be any library formed by the expression of a DNA library of the present invention.

A peptide library member can be defined as an amino acid chain of variable composition of at least two amino acids in length, or part or all of a naturally occurring protein such as an enzyme, a binding molecule such as a receptor or an antibody or a fragment thereof. A suitable peptide library member may be a peptide having random amino acid composition. The peptide of variable or random composition may be flanked by known amino acid sequences a the N- and/or C-terminus to constrain the structure. These known sequences may vary in length. The peptide of variable or random composition may be inserted at various positions in a known protein scaffold, such as a receptor or antibody or other protein or fragment thereof. The peptide may be inserted into the same protein scaffold once or more than once, for example two or more times.

A DNA construct according to the present invention may comprise DNA encoding a library member peptide and means for the encoded peptide to bind to the encoding DNA construct. In addition to DNA encoding a library member peptide, a suitable DNA construct of the invention comprises at least a DNA target sequence and DNA encoding a peptide capable of binding directly or indirectly to the DNA target sequence.

According to the present invention, the DNA construct and the encoded protein are chosen to have cis-activity. That is, the encoded protein has the ability to bind specifically to the DNA molecule which encoded it. For example, cis-activity may function to allow the encoded DNA binding peptide to bind specifically (directly or indirectly) to the target sequence of the DNA construct which encoded it rather than to the target sequence of another DNA construct.

In some cases, cis activity may be provided due to the presence of a DNA element that directs cis-activity. i.e. that allows or forces the protein encoded by the DNA construct to have cis-activity, and therefore to bind to its encoding sequence. In other cases, a separate DNA element per se may not be required where the nature of the encoding DNA inherently confers cis activity on the encoded peptide.

A DNA element that directs cis-activity may be provided in the DNA construct together with the DNA encoding a peptide that interacts with that cis element. For example, in the case of the cis element from the repA system discussed below, DNA encoding a fragment of the repA sequence comprising at least 20 amino acids from the C terminal of repA may be provided along with the cis DNA element. It may be possible to confer cis activity upon a DNA binding peptide that is not normally cis-acting by including in the DNA construct such a DNA element and any further sequences necessary for its action. For example, DNA encoding a peptide that interacts with the cis element used may be included in the DNA construct.

Alternatively, a peptide that interacts with the cis element may be part of the DNA binding peptide. For example, the DNA binding peptide may be repA which comprises the sequence that interacts with the repA cis element. Alternatively, the DNA binding peptide may bind to its encoding DNA in cis without the need for a separate cis element.

A suitable DNA element may be any element which allows or directs cis-activity. Such a DNA element may act, for example, by interacting with the machinery involved in translation and transcription of the DNA construct to delay the production and release of the encoded peptide.

Any DNA element which allows the encoded peptide to bind specifically to the DNA molecule which encoded it may be used as a DNA element according to the present invention. One example of a suitable DNA element is that of the repA-cis system described in more detail below. In that system, RNA polymerase is paused by loops in the 5' cis sequence prior to the rho dependent termination of transcription. The action of the DNA element therefore allows the encoded binding peptide to bind to the DNA target sequence in the construct from which it was produced.

Preferably, the cis DNA element will be located 3' in the DNA construct to the library member peptide and to the peptide or protein capable of binding to the DNA target sequence. This means that these sequences may be transcribed and translated before the RNA polymerase reaches the cis acting sequence.

According to the present invention, the binding peptide may be linked to the DNA construct directly or indirectly. In the case of direct binding, the binding peptide binds directly and non-covalently to the DNA target sequence. In the case of indirect binding, the link between the binding peptide and DNA construct is provided by a further molecule. Such a molecule, for example a bifunctional agent as described below, will associate with both the peptide and the DNA target sequence.

A suitable DNA construct may comprise further sequences, for example suitable promoter sequences to allow expression of the encoded peptide.

One example of a system in which cis-activity exists is the a cis acting incompatibility group plasmid replication protein, termed repA, system. Aspects of this system may be utilised in the present invention as explained below.

Numerous plasmids include sequences encoding repA and cis DNA elements. The repA sequence and cis DNA element present in a DNA construct of the invention may be derived from the same plasmid strain or may be derived from different plasmid strains.

It is believed that the repA-cis system acts as shown in FIG. 1. Briefly, RNA polymerase is paused by loops in the 5'-CIS sequence prior to rho dependent termination of transcription. This allows transient C-terminal repA peptide interaction with CIS, and possibly DNA bending. RepA peptide then binds to ori, which is a defined distance away from the terminal amino acid of the repA coding sequence (Prazkier et al. 2000 J. Bacteriology 182: 3972-3980; Praszkier and Pittard 1999 J. Bacteriol. 181: 2765-2772 Masai and Arai. 1988 Nucleic Acids Res. 16: 6493-6514).

The compatibility of a RepA sequence from a plasmid with a cis sequence from another plasmid can be readily determined by monitoring for the interaction of RepA with the selected cis sequence.

Suitable repA proteins and sequences and cis DNA elements include those of the IncI complex plasmids or the IncF, IncB, IncK, IncZ and IncL/M plasmids, which are distantly related at the DNA level, but which control plasmid replication through the action of the cis acting repA protein (Nikoletti et al. 1986 J. Bacteriol. 170:1311-131S; Prazkier J. et al. 1991 J. Bacteriol. 173: 2393-2397). Specific plasmids which may be used to provide these sequences include the R1 plasmid of the IncII incompatibility group and the incB plasmid pMU720 (described by Praskier J. & Pittard J. 1999 Role of CIS in replication of an IncB plasmid. J. Bacteriol. 181: 2765-2772). The DNA and amino acid sequences of repA derived from the R1 plasmid of IncII are given in SEQ ID Nos: 15 and 16. The DNA sequence of the cis DNA element from the R1 plasmid of IncII is given in SEQ ID NO: 17. Typically, the cis element is 150 to 200 nucleotides in length. Shorter or larger sequences may be used, so long as the sequence maintains the ability to interact with RepA and display cis activity. Minor variations, such as substitutions or deletions within the cis sequence are also contemplated such as modifications at 1, 5, 10 up to 20 nucleotides within the wildtype cis sequence.

The cis element is required for cis activity of the repA protein (Praszkier and Pittard 1999 J. Bacteriol. 181: 2765-2772). The cis DNA element should therefore also be located 3' in the DNA construct to the DNA encoding the repA sequence. On reaching the cis sequence, the RNA polymerase will be paused, allowing the encoded protein to bind the DNA target sequence.

In one embodiment of the present invention, the DNA binding protein itself comprises RepA or a fragment or variant thereof capable of DNA binding, including at least the 20 C-terminal amino acids of RepA capable of binding to the cis DNA element. In this embodiment, the DNA target sequence comprises an ori sequence, for example the oriR sequence. In alternative aspects of the present invention, the DNA binding protein is provided by an alternative protein with the relevant DNA target sequences recognised by such binding protein incorporated into the sequence. In each of these embodiments, DNA-protein binding is direct in that the peptide encoded by the DNA construct will bind directly to the encoding DNA construct. In alternative aspects of the invention, as described in more detail below the DNA-protein binding may be indirect through the use of a peptide tag-DNA tag, bifunctional agent and/or suitable linkers.

In one aspect, the same sequence may therefore provide both the peptide capable of binding the DNA target sequence and the C terminal amino acids of repA. Such a sequence may be or may comprise a complete repA sequence, or a fragment or variant thereof of a repA sequence which retains the ability to bind to the DNA target sequence used. Where the repA acts as a DNA binding protein, both cis and ori sequences (Praszlkier and Pittard 1999 J. Bacteriol. 181: 2765-2772) are required for cis activity (cis) and DNA binding (ori). In this aspect, therefore, the DNA target sequence is an ori sequence and the peptide or protein capable of binding said target is a repA protein. The position of ori in the DNA constructs of the invention may be varied. As described earlier, suitable repA, cis and ori sequences may be provided by one or more plasmids. For example, suitable sequences may be provided from the IncI complex plasmids or the IncF, IncB, IncK, IncZ and IncL/M plasmids. The DNA sequence of the ori from the R1 plasmid of IncII is given in SEQ ID NO: 18. This sequence, or a fragment thereof may be included in a DNA construct of the invention. A DNA construct of the invention may include a complete ori sequence or may include a fragment thereof which is capable of being bound by the repA protein being used.

The RepA protein used in accordance with the present invention may also comprise a fragment or variant of RepA, so long as such variant or fragment of RepA maintains the ability to bind to the selected ori sequence. Such variant or fragment of RepA may include substitutions, for example, at 1, 2, 3 up to 20 amino acids within the RepA sequence so long as such variants maintain the ability to bind to the ori sequence. A suitable fragment of RepA is an ori binding sequence of RepA. Ori sequences include those which are present in wild type plasmids as described above. Typically, such an ori sequence is 170 to 220 nucleotides in length. Fragments and variants of wild type ori sequences may also be used, so long as such ori sequences maintain the ability to be recognised by RepA. Further cis acting members of the RepA protein family can be used. For example, the RepA family of proteins is found on plasmids with a broad host range i.e. one RepA plasmid may be found in different bacterial species. Isolation of a repA family plasmid from (for example) a thermophilic, sulfophilic, halophilic or acidophilic bacterium would provide repA-cis-ori DNA that could be used under the current invention at elevated temperatures or extremes of salt, pH or sulphur concentrations. Such members of the RepA family would be advantageous in isolating library members that can bind to target molecules under such extreme conditions. Suitable ori sequences for use in combination with selected RepA proteins can readily be determined by monitoring for the interaction of RepA with such an ori sequence.

The basic principle of the invention may therefore be described with reference to the repA/cis/ori system, as shown in FIG. 1. This shows an example of a DNA construct of the invention. This construct comprises, from 5' to 3', a promoter sequence, a sequence encoding a library member peptide, a sequence encoding a repA protein, a cis DNA element and an ori sequence. Briefly, the DNA sequence is transcribed from the promoter by RNA polymerase to RNA. The rho dependent termination function present in the cis DNA element causes the RNA polymerase to pause at this part of the sequence. This allows the repA protein and the library peptide to be translated. The repA protein is then able to bind to the ori sequence, linking the encoded protein to the encoding DNA construct.

In one preferred embodiment, library member DNA sequence(s) are fused to the repA, cis and ori DNA of the IncFII plasmid R1 (Masai H et al. 1983 Proc Natl Acad Sci USA 80: 6814-6818). In this embodiment, the library member DNA sequence(s) of interest may be joined by a region of DNA encoding a flexible amino acid linker, to the 5'-end of the repA DNA, under the control of an appropriate promoter and translation sequences for in vitro transcription/translation. Many suitable promoters are known to those skilled in the art, such as the araB, tac promoter or the T7, T3 or SP6 promoters, amongst others. The promoter should be upstream of the polypeptide sequence to be expressed.

The repA family of proteins is used herein by way of example, not limitation. Other unrelated non-covalently binding cis acting DNA binding proteins could be used in this invention.

Figure 2:
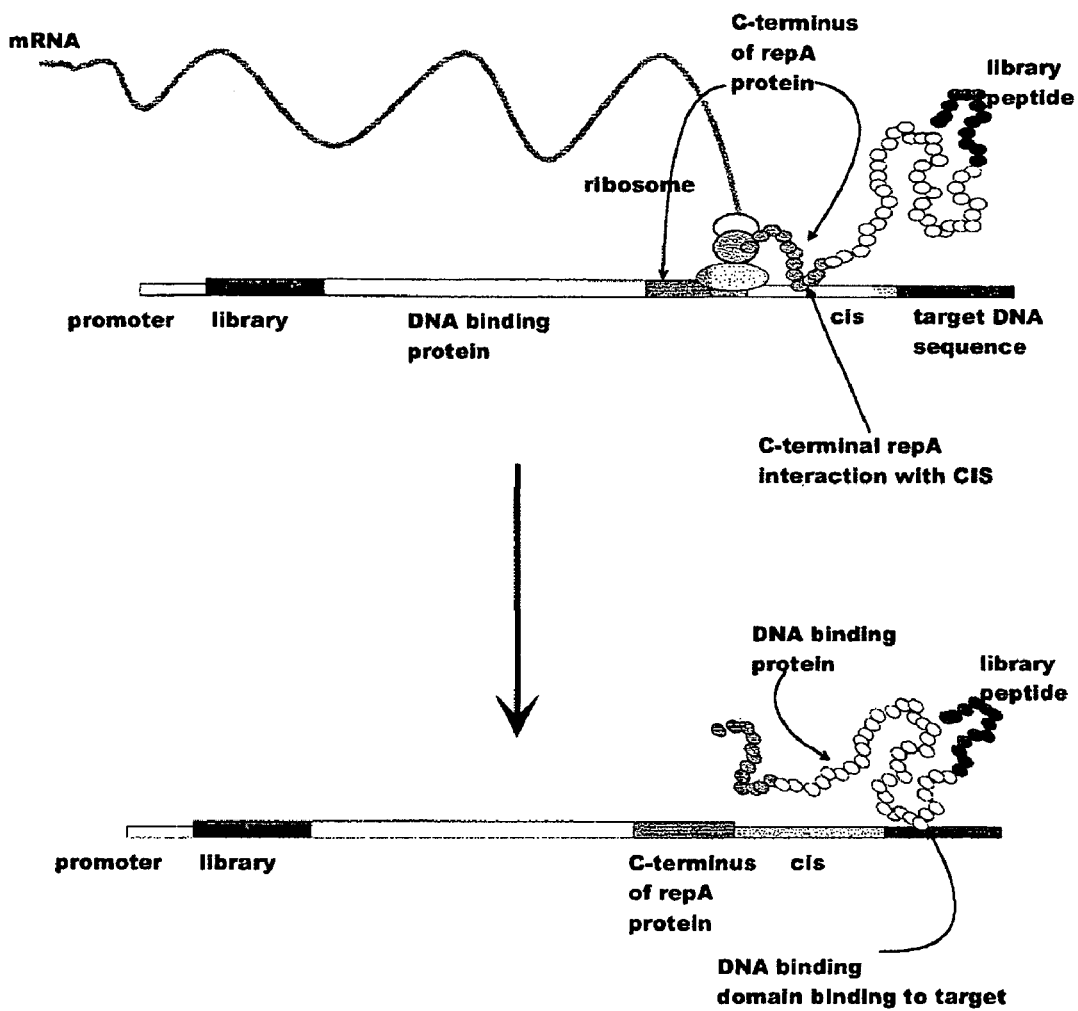
FIG. 2 give a schematic representation of a method of the invention by which a DNA binding protein may be converted to a cis-acting DNA binding protein.

In a further embodiment, non-cis acting DNA binding proteins may be converted to having cis-activity (see FIG. 2). This may be achieved by using such proteins, capable of binding the DNA target sequence, either directly or indirectly in combination with sequences which can confer cis-activity upon them. Cis activity may be conferred on a binding protein that does not normally act in cis by including in the DNA construct a DNA element that directs cis-activity such as the cis element of the repA system. Such an element may be included to ensure that the DNA binding by the DNA binding protein is cis, that is, an encoded DNA binding protein will bind to the DNA construct from which it has been transcribed and translated.

In one embodiment, a suitable DNA construct may therefore comprise the DNA element that directs cis-activity (the cis DNA element) from the repA system. Such an element may further comprise DNA encoding a portion of the C-terminal end of RepA, preferably at least 20 amino acids, more preferable 30 amino acids, up to 40, 50, 60 or 70 amino acids from the C-terminal portion of repA, wherein said fragment of repA is capable of interacting with the DNA element within the construct. In a further example, proteins such as the cis acting transposases, Tn5 and IS903, amongst others, could be used under the current invention (McFall E. J Bacteriol. 1986 August 167:429-432; Derbyshire K M & Grindley N D. Mol Microbiol. 1996 September 1:1261-72.). DNA encoding sequences of the present invention may comprise wild type sequences encoding the desired fragment of RepA, degenerate sequences encoding fragments of wild type RepA or sequences encoding variants of such fragments of RepA which maintain the ability to interact with the cis element incorporated into the DNA construct. Such variants may include substitution of 1, 2, 3 or 4 amino acids within the 20 amino acid C-terminal of RepA.

The repA family of proteins is used herein be way of example, not limitation. Any DNA element capable of conferring cis-activity on a non-cis acting protein could be used.

Any non-cis acting protein may be converted in this way. By way of example, not exclusion, the estrogen receptor DNA binding domain (DBD) can be converted into a cis acting DNA binding protein. The oestrogen receptor DNA binding domain fragment (amino acids 176-282) has been expressed in E. coli and shown to bind to the specific double stranded DNA oestrogen receptor target HRE nucleotide sequence, with a similar affinity (0.5 nM) to the parent molecule (Murdoch et al. 1990, Biochemistry 29: 8377-8385; Mader et al., 1993, DNAs Research 21: 1125-1132). In one embodiment, the DNA encoding this sequence is fused, preferably at the 3'-end, to the DNA encoding at least the last 20 amino acids of repA, the cis DNA element, and the DNA up to the ori sequence followed by the estrogen receptor target recognition sequence (5'-TCAGG TCAGA GTGAC CTGAG CTAAA ATAAC ACATT CAG-3', SEQ ID NO: 14) which replaces the repA ori recognition sequence. The DNA sequence(s) of interest may then be joined by a region of DNA encoding a flexible amino acid linker, to the 5'-end of to the estrogen receptor DNA fragment, under the control of an appropriate promoter and translation sequences for in vitro transcription/translation. Expression of this polypeptide directs the estrogen receptor DBD to its target sequence, present in place of the normal ori sequence, on the DNA encoding that polypeptide. Protein-DNA complexes can then be isolated by capture on a target protein. Unbound protein-DNA complexes can be washed away, allowing enrichment for DNA encoding peptides or proteins of interest, which can then be recovered by PCR, and enriched further by performing several further cycles of in vitro expression and protein-DNA complex capture using methods described previously.

It will be clear that this approach will apply to other DNA binding proteins simply by using the cis DNA element and a sequence encoding at least the C-terminal 20 amino acids of repA, or equivalent elements from a different cis-acting system in the DNA constructs.

Figure 3:
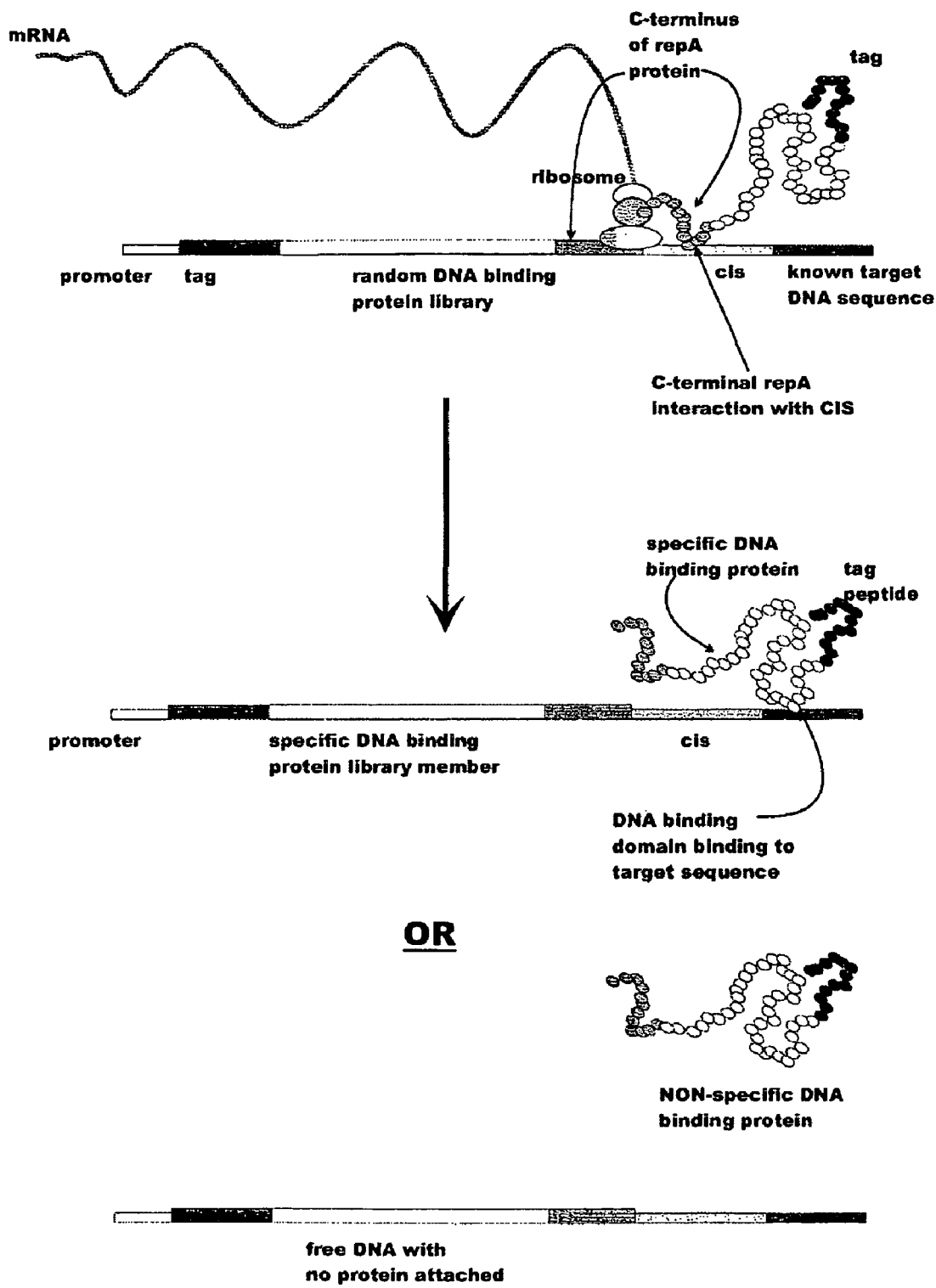
FIG. 3 gives a schematic representation of how a target sequence specific DNA binding protein may be isolated from a library of the invention.

In another embodiment, libraries of randomized DNA binding proteins, such as zinc finger proteins, helix-loop-helix proteins or helix-turn-helix proteins by way of example, may be screened for specific binding to a target sequence of interest (see FIG. 3). In this embodiment, the ori recognition sequence of repA may be replaced by a target sequence of interest, and the majority of the repA coding sequence by a library of randomised zinc finger proteins. The DNA binding proteins therefore act as both the library member peptides and the proteins capable of binding the DNA target sequence in this aspect. The DNA encoding each zinc finger protein, may additionally be joined, at the 5'-end, to a peptide tag sequence which can be recognized by an another capture protein such as an antibody, and at the 3'-end, to the DNA encoding at least the last 20 amino acids of repA, the cis DNA element, and the DNA up to the ori sequence followed by the target sequence of interest. Expression of this polypeptide directs the zinc finger protein to the target sequence of interest, present in place of the normal ori sequence, on the DNA encoding that polypeptide. Binding to the target sequence will only occur if the randomised zinc finger domain is capable of binding to the sequence of interest. Protein-DNA complexes can then be isolated by capture with a binding protein which recognizes the peptide tag at the N-terminus of the fusion protein polypeptide. Unbound DNA can be washed away, allowing enrichment for DNA encoding zinc finger proteins capable of binding the target sequence, which can then be recovered by PCR, and enriched further by performing several further cycles of in vitro expression and protein-DNA complex capture.

Figure 4:
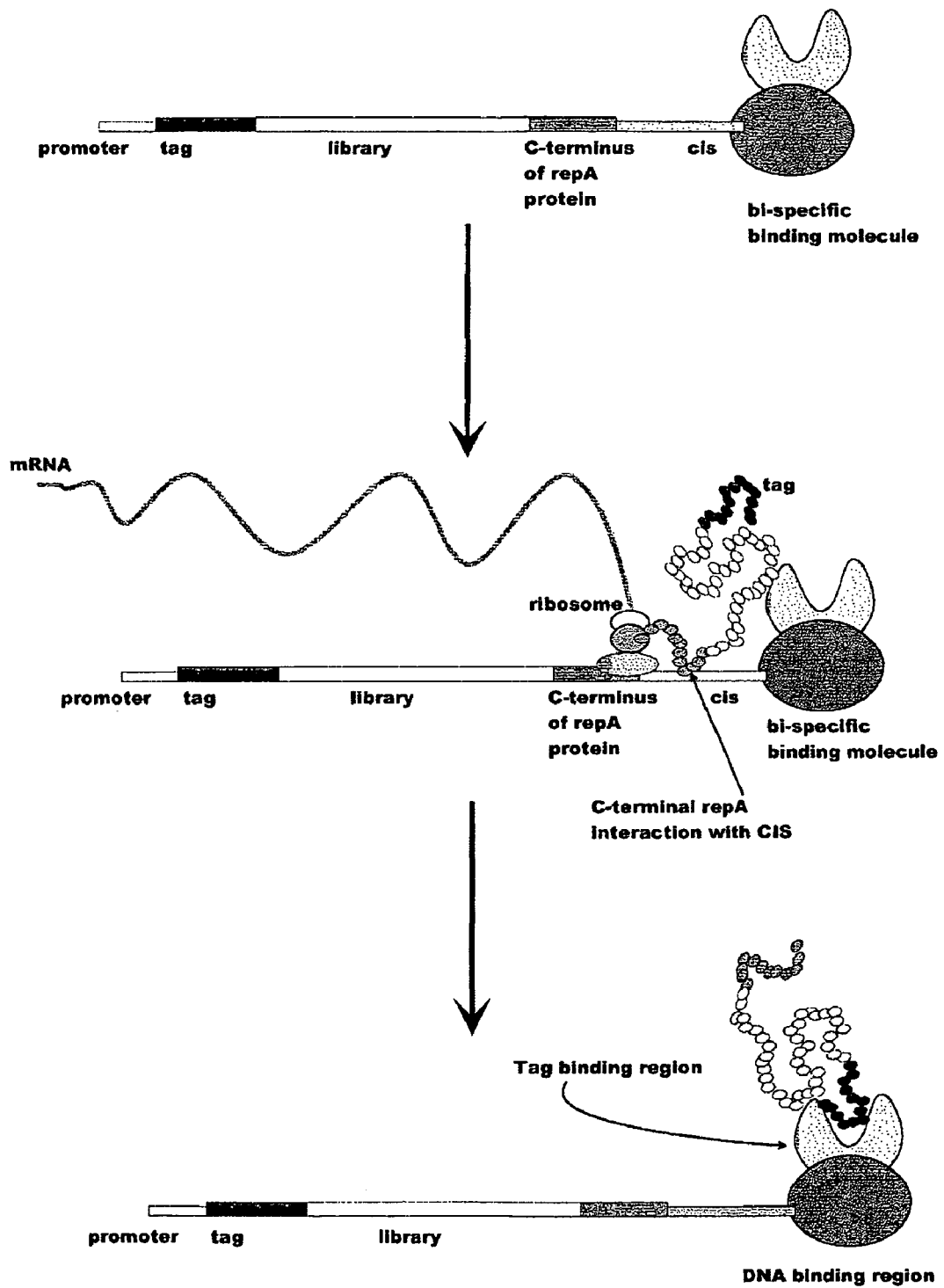
FIG. 4 gives a schematic representation of how a library protein may be linked to its coding DNA through cis action and the use of a bi-specific binding molecule.

As explained above, the binding peptide may bind directly to the DNA target sequence, for example in the case of a DNA binding protein-target sequence pair, or it may bind indirectly to the DNA target sequence, for example via a bifunctional agent and optionally a DNA tag (see FIG. 4):

In one embodiment, DNA encoding a peptide tag which is not able to bind directly to the DNA target sequence is joined to the 5'-end of library member DNA sequence(s) of interest, optionally by a region of DNA encoding a flexible amino acid linker, under the control of an appropriate promoter and translation sequences for in vitro transcription/translation. This forms the DNA encoding the binding peptide, as the encoded peptide is linked indirectly to the DNA target sequence. Optionally at the 3'-end of the library member DNA sequence is the DNA encoding at least the last 20 amino acids of repA and the cis DNA element, but not the ori target sequence of repA. The DNA target sequence may be or may comprise a DNA tag. Such a DNA tag may be a single modified base. For example, when preparing the library DNA construct containing the elements described, the DNA may be tagged at the 3'-end with, by way of example not limitation, molecules such as fluorescein or biotin.

Prior to in vitro expression, the library DNA fragments may be mixed with a bifunctional agent, one function of which is to recognize and bind to the target sequence which may be at the 5' end of the DNA, in a ratio of one DNA fragment: one bifunctional molecule. The other functional element of this bifunctional agent is a binding agent that can recognize and bind to the peptide tag which may be encoded at the 5'-end of the DNA fragment. By way of example not exclusion, the bifunctional agent can be composed of an Fab fragment recognizing the fluorescein or biotin tag on the DNA, and another Fab fragment recognizing the peptide tag encoded in the DNA. It is clear to those skilled in the art that this bifunctional agent can be made by many different methods such as chemically cross-linking the two elements, or by expressing the two elements as a fusion protein, or as a bi-specific antibody. Said methods of creating a bifunctional agent are given by way of example not exclusion.

The bifunctional agent may be bound to the DNA construct prior to expression of the encoded peptide or may be provided during expression.

The fusion protein is then transcribed and translated from the DNA construct while bound to the bifunctional agent. The peptide tag is translated first, and can be bound by the second element of the bifunctional agent, prior to release of messenger RNA or RNA polymerase from the DNA. This creates a functional protein-DNA complex where both expressed polypeptide and DNA encoding that peptide are linked through the bifunctional agent. The peptide tag molecule is therefore linked indirectly, but specifically, to the DNA target (tag). By linking the protein to the DNA construct in this way, it is possible to screen for a protein having particular properties, as described below, and then to identify the encoding DNA which is linked to that protein. By using a bifunctional agent rather than covalent binding between the protein and DNA, the DNA construct may be more easily separated form the protein without the risk of damaging the DNA.

Protein-DNA complexes can then be isolated by capture of a target protein. Unbound protein-DNA complexes can be washed away, allowing enrichment for DNA encoding peptides or proteins of interest, which can then be recovered by PCR, and enriched further by performing several further cycles of in vitro expression and protein-DNA complex capture using methods described previously.

Additionally, under this embodiment, the DNA can be bound directly, for example by covalent binding, to a bifunctional agent such as a polymer. Such a polymer can contain more than one binding element that could recognise the peptide tag, allowing multivalent display of a peptide expression library molecule in a unit containing the DNA encoding the displayed peptide. By way of example, not limitation, said polymers can be composed of polyethylene as well as other polymeric compounds, capable of being fused to DNA. The DNA construct of the invention may therefore be provided bound to such a bifunctional agent, or bound to a DNA tag as described above which is capable of being bound by such a bifunctional agent.

In all embodiments of the invention, the DNA constructs include appropriate promoter and translation sequences for in vitro transcription/translation. Any suitable promoter can be used, such as the ara B, tac promoter, T7, T3 or SP6 promoters amongst others. The promoter is placed so that it is operably linked to the DNA sequences of the invention such that such sequences are expressed.

The DNA encoding the library member peptides may be produced by any sourcible means. In particular, such DNA may comprise DNA isolated from cDNA, obtained by DNA shuffling, and synthetic DNA.

The DNA construct may also encode amino acid linkers within the expressed fusion protein. In particular, a flexible amino acid linker may be included to join the DNA binding peptide/RepA to the library member peptide.

According to the invention, with reference to this preferred embodiment, peptide or protein expression libraries, linked to the DNA encoding them, can be generated and peptides with the desired activity selected by the following steps:

Constructing a Library of Fusion Proteins

A DNA library of peptides or proteins may be fused to DNA encoding a peptide capable of binding to the DNA target sequence, such as a cis acting DNA binding protein DNA, by a region of DNA encoding a flexible amino acid linker, under the control of an appropriate promoter and with a translation, or ribosome binding site, start and stop codons, in a manner suitable for in vitro expression of the peptide library members and binding proteins. In the example of the repA protein, the DNA (such as DNA) library members are fused to the repA DNA binding protein DNA, or a fragment thereof. The cis and ori sequences may be included in the construct downstream of the other elements. In the case of a DNA library, said DNA constructs are designed to be suitable for in vitro transcription and translation.

Expression and cis Binding of DNA Library Fusion Proteins

In order to allow cis activity, a coupled bacterial transcription/translation environment such as the S30 extract system (Zubay, G. 1973. Ann. Rev. Genet. 7: 267) may be used. Expression of the peptide, such as the DNA library member peptide-repA fusion protein, in this environment, will result in binding of the fusion protein to the DNA encoding that fusion protein, provided that both cis and ori sequences are present. When libraries of peptide-repA fusion proteins are expressed in this manner, this process results in the production of libraries of protein-DNA complexes where the protein attached to the DNA is encoded by that fragment of DNA from which it was expressed, thereby allowing subsequent selection of both peptides or protein of interest, and the DNA encoding said peptides. The complexity of these libraries is enhanced by the in vitro nature of the method, libraries of at least $10^{10}$-$10^{14}$ DNA fragments, if not even larger libraries, can easily be generated.

Compounds that prevent nuclease activity, or reduce non-specific DNA-protein or protein-protein interactions may be added during this transcription/translation reaction and cis-binding. Examples of suitable compounds include detergents and blocking proteins such as bovine serum albumin (BSA).

Selection of Peptide of Interest

As in vitro peptide expression library produced by a method of the present invention may be used to screen for particular members of the library. For example, the library may be screened for peptides with a particular activity or a particular binding affinity. Protein-DNA complexes of interest may be selected from a library by, for example, affinity or activity enrichment techniques. This can be accomplished by means of a ligand specific for the protein of interest, such as an antigen if the protein of interest is an antibody. The ligand may be presented on a solid surface such as the surface of an ELISA plate well, or in solution, for example, with biotinylated ligand followed by capture onto a streptavidin coated surface or magnetic beads, after a library of protein-DNA complexes had been incubated with the ligand to allow ligand-ligand interaction. Following either solid phase or in solution incubation, unbound complexes are removed by washing, and bound complexes isolated by disrupting ligand-ligand interactions by altering pH in the well, or by other methods known to those skilled in the art such as protease digestion, or by releasing the DNA directly from the complexes by heating or phenol-chloroform extraction to denature the repA-ori DNA binding. DNA can also be released by one of the methods above, directly into PCR buffer, and amplified. Alternatively, DNA may be PCR amplified directly without release from the complexes. Optionally, DNA not bound by the binding for example repA protein, can be protected from degradation by non-specific DNA binding proteins such as histones, by way of example. It will be clear to one skilled in the art that many other non-specific DNA binding proteins could be used for this purpose. Further, compounds that prevent nuclease activity, or reduce non-specific DNA-protein or protein-protein interactions may be present during the selection process. Examples of suitable compounds include detergents, blocking proteins such as found in milk powder or bovine serum albumin (BSA), heparin or aurintricarboxylic acid.

Recovering bound complexes, reamplifying the bound DNA, and repeating the selection procedure provides an enrichment of clones encoding the desired sequences, which may then be isolated for sequencing, further cloning and/or expression. For example, the DNA encoding the peptide of interest may be isolated and amplified by, for example PCR. In one embodiment, repeated rounds of selection and DNA recovery may be facilitated by the use of sequential nesting of PCR primers. DNA ends are generally damaged after multiple PCR steps. To recover DNA from such damaged molecules required the primers to be annealed away from the ends of the DNA construct, thereby sequentially shortening the construct with every round of selection.

In one aspect, the DNA construct and/or the encoded protein may be configured to include a tag. Such a peptide or DNA tag, for example as described above, may be used in the separation and isolation of a library member of interest. Such a tag may also be used to hold the library members, for example on a solid support for use in the screening methods described herein.

It can therefore be seen that the screening methods of the present invention may include the further step of selecting and isolating the relevant library member peptide, allowing the peptide exhibiting the desired properties, and also the DNA encoding that peptide, to be identified and purified.

The invention therefore encompasses peptides and DNAs that have been identified by a method of the invention. These peptides and DNAs may be isolated and/or purified. The peptides or DNAs isolated by a method of the invention may be modified, for example by deletion, addition or substitution of amino acids or nucleotides. Suitable modified peptides or DNAs may show at least 50%, at least 75% at least 90%, at least 95% or more amino acid or nucleotide sequence identity to the peptide or DNA isolated by the method of the invention. Peptides identified by a method of the invention may be modified for delivery and/or stability purposes. For example, such peptides may be pegylated (attached to polyethylene glycol) to prolong serum half life or to prevent protease attack. Peptides identified by a method of the invention may be modified in other display systems such as phage display or by synthesising and screening peptide variants. A collection of such modified sequences may form a new library which may be incorporated into constructs of the invention and further screened to find, for example, a variant sequence showing improved binding to a particular ligand. Thus in one embodiment, a library of peptides for use in the methods of the invention may be a library of structurally related peptides.

Alternatively, a library of essentially random peptide sequences may be used. Numerous types of libraries of peptides fused to the cis acting DNA-binding protein can be screened under this embodiment including:

(i) Random peptide sequences encoded by synthetic DNA of variable length.

(ii) Antibodies or antibody fragments, for example single-chain Fv antibody fragments. These consist of the antibody heavy and light chain variable region domains joined by a flexible linker peptide to create a single-chain antigen binding molecule.

(iii) Random cDNA fragments of naturally occurring proteins isolated from a cell population containing an activity of interest.

(iv) Random peptide sequences inserted into, or replacing a region of a known protein, whereby the known protein sequence acts as a scaffold, which constrains the random peptide sequence. Many, such scaffolds have been described, by way of example, not exclusion, CTLA-4 (WO 00/60070), has been used as a scaffold for peptide libraries.

In another embodiment the invention concerns methods for screening a DNA library whose members require more than one chain for activity, as required by, for example, antibody Fab fragments for ligand binding. In this embodiment heavy or light chain antibody DNA is joined to a nucleotide sequence encoding a DNA binding domain of, for example, repA. Typically the unknown antibody DNA library sequences for either the heavy (VH and CH1) or light chain (VL and CL) genes are inserted in the 5' region of the repA DNA, behind an appropriate promoter and translation sequences. Thus, repA fused to a DNA library member-encoded protein is produced bound to the DNA encoding that protein. The second known chain, encoding either light or heavy chain protein, is expressed separately either:

(a) from the same DNA fragment containing the repA and the first polypeptide fusion protein library, or (b) from a separate fragment of DNA present in the in vitro transcription/translation reaction.

The known chain associates with the library of unknown fusion proteins that are fused to the repA protein and thereby bound to the DNA for the unknown chain. The functional Fab library can then be selected by means of a ligand specific for the antibody.

The DNA identified by a screening method of the invention, e.g. the DNA encoding the selected library member peptide, may be cloned into a vector. In one embodiment, the DNA identified by a method of the invention is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for protein expression. Other suitable vectors would be apparent to persons skilled in the art. By way of further example in this regard we refer to Sambrook er al. 1989.

The vectors may be for example, plasmid, virus or phage vectors provided with a origin of replication, optionally a promoter for the expression of the said DNA and optionally a regulator of the promoter. The vectors may contain one or more selectable marker genes, for example an ampicillin resistence gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vitro, for example in a method of gene therapy.

Promoters and other expression regulation signals may be selected to be compatible with the host cell for which expression is designed. For example, yeast promoters include S. cerevisiae GAL4 and ADH promoters, S. pombe nmt1 and adh promoter. Mammalian promoters include the metallothionein promoter which can be induced in response to heavy metals such as cadmium. Viral promoters such as the SV40 large T antigen promoter or adenovirus promoters may also be used. All these promoters are readily available in the art.

Mammalian promoters, such as $\beta$-actin promoters, may be used. Tissue-specific promoters are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art.

The vector may further include sequences flanking the polynucleotide of interest giving rise to polynucleotides which comprise sequences homologous to eukaryotic genomic sequences, preferably mammalian genomic sequences, or viral genomic sequences. This will allow the introduction of the polynucleotides of the invention into the genome of eukaryotic cells or viruses by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors and retroviruses, including lentiviruses, adenoviruses, adeno-associated viruses and HPV viruses. Gene transfer techniques using these viruses are known to those skilled in the art. Retrovirus vectors for example may be used to stably integrate the polynucleotide giving rise to the polynucleotide into the host genome. Replication-defective adenovirus vectors by contrast remain episomal and therefore allow transient expression.

Such expression vectors may be used to identify ligands of interest, i.e. molecules that bind to the peptide library member by standard binding assays such as ELISA, or enzymatic assays where appropriate substrates give, for example a colour change, light emission or fluorescence. Other functional assays could be used, where available.

In an alternative embodiment, a DNA identified by a method of the invention may be cloned into a non-expression vector. Such a vector may be used to further characterise the DNA, for example by sequencing.

Alternatively, ligands of interest may be identified without cloning. Examples of suitable methods include the in vitro expression of individual DNA sequences recovered from a screening method of the invention, and sequencing of individual DNAs recovered from such a screening method. Such individual DNA sequences may optionally be amplified.

The invention also includes cells that have been modified to express a peptide identified by a method of the invention, for example by introducing an expression vector as described above into the cell. Such cells include transient, or preferably stable higher eukaryotic cell lines, such as mammalian cells or insect cells, using for example a baculovirus expression system, lower eukaryotic cells, such as yeast or prokaryotic cells such as bacterial cells. Particular examples of cells which may be modified be insertion of vectors encoding for a peptide identified by a method of the invention include mammalian HEK293T, CHO, HeLa and COS cells. Preferably the cell line selected will be one which is not only stable, but also allows for mature glycosylation and cell surface expression of the peptide. Expression may be achieved in transformed oocytes. A peptide identified by a method of the invention may be expressed in cells of a transgenic non-human animal, preferably a mouse. A peptide identified by a method of the invention may also be expressed in *Xenopus laevis* oocytes or melanophores.

In order that the invention is more fully understood, embodiments will now be described in more detail by way of example only and not by way of limitation with reference to the figures below.

Examples of some of the embodiments of the invention are given below:

Materials and Methods

The following procedures used by the present applicant are described in Sambrook, J., et al. 1989 supra.: analysis of restriction enzyme digestion products on agarose gels, DNA purification using phenol/chloroform stock solutions, preparation of phosphate buffered saline.

General purpose reagents were purchased from SIGMA-Aldrich Ltd (Poole, Dorset, U.K.). Oligonucleotides were obtained from SIGMA-Genosys Ltd (Cambridgeshire, U.K.). Amino acids, and S30 extracts were obtained from Promega Ltd (Southampton. Hampshire, U.K.). Deep Vent and Taq DNA polmierases were obtained from New England Biolabs (Cambridgeshire, U.K.). Taqplus DNA polymerase was obtained from Stratagene Inc. (Amsterdam, Netherlands). GeneClean DNA gel purification hits were obtained from BIO101 (La Jolla, Calif., U.S.A.), anti-human IgK antibodies from Immunologicals Direct Ltd (Oxfordshire, U.K.), anti-c-myc polyclonal from Vector Labs Inc (Cambridgeshire U.K.), and anti-V5 antibody from Abcam Ltd (Cambridgeshire U.K.). Superblock blocking agent was obtained from Perbio Science (Cheshire, U.K.).

EXAMPLE 1

Isolation of Specific cis Acting Protein-DNA Complexes

The in vitro expression constructs were prepared by sequentially adding the TAC promoter, the c-myc epitope, either the human kappa constant region or the V5 epitope to the RepA-CIS-ORI region, by PCR amplification. Such constructs can be prepared by many methods known to one skilled in the art, for example, by amplifiying different fragments of DNA followed by assembly PCR. In this example, the initial amplification template was the R1 plasmid which contains the RepA-CIS-ORI region (Masai, H. and Arai, K.(1988). DNAs Res. 16, 6493-6514).

(a) Primary amplification. The RepA-CIS-ORI region was PCR amplified from a single colony of the strain ECO K12 harbouring plasmid R1 using 12.5 pmol of each of the primers REPAFOR (SEQ ID 01) and ORIREV (SEQ ID 02) in a 50 µl reaction containing 0.25 mM dNTPs, 2.5 units Taqplus Precision DNA polymerase, 1×PCR reaction buffer (Stratagene Inc, Amsterdam, Netherlands). The REPAFOR primer anneals to the 5'-end of the RepA coding region. The ORIREV primer anneals to the 3'-end of the non-coding ORI region.

PCR reactions were carried out on a Eppendorf plaster Cycler for 1 circle of 4 minutes and 15 seconds at 94° C. followed by 30 cycles of 94° C., 45 seconds; 60° C., 45 seconds; 72° C., 45 seconds, followed by a single cycle 10 minutes at 72° C. Reaction products were electrophoresed on an agarose gel, excised and products purified from the gel into 40 µl sterile water using a Geneclean II kit according to the manufacturers instructions (Bio101, La Jolla, Calif., U.S.A.).

(b) Secondary amplification. One µl (500 pg) of 100 times diluted gel-purified primary reaction product was re-amplified using 12.5 pmol of each of the primers CKREPFOR (SEQ ID 03) and ORIREV (SEQ ID 02) in a 50 µl reaction containing 0.25 mM dNTPs, 2.5 units Taqplus Precision DNA polymerase, and 1×PCR reaction buffer (Stratagene Inc, Amsterdam, Netherlands). The CKREPFOR primer anneals to the 5'-end of the primary reaction product and appends the 3' part of the kappa constant region DNA. The ORIREV primer anneals to the 3'-end of the primary reaction product.

PCR reactions were carried out on a Eppendorf Master Cycler for 1 cycle of 2 minutes and 15 seconds at 94° C. followed by 30 cycles of 94° C., 45 seconds; 60° C. 45 seconds; 72° C. 2 minutes, followed by a single cycle 10 minutes at 72° C. Reaction products were electrophoresed on an agarose gel, excised and products purified from the gel into 40 µl sterile water using a Geneclean II kit according to the manufacturers instructions (Bio101, La Jolla, Calif., U.S.A.).

(c) Third amplification. One µl (500 pg) of 100 times diluted gel-purified primary reaction product was re-amplified using 12.5 pmol of each of the primers V5REPFOR (SEQ ID 04) and ORIREV (SEQ ID 02) in a 50 µl reaction containing 0.25 mM dNTPs, 2.5 units Taqplus Precision DNA polymerase, and 1×PCR reaction buffer (Stratagene Inc, Amsterdam, Netherlands). The V5REPFOR primer anneals to the 5'-end of the primary reaction product and appends the 3' part of the V5 epitope DNA. The ORIREV primer anneals to the 3'-end of the primary reaction product.

PCR reactions were carried out on a Eppendorf Master Cycler for 1 cycle of 2 minutes and 15 seconds at 94° C. followed by 30 cycles of 94° C., 45 seconds; 60° C., 45 seconds; 72° C., 2 minutes, followed by a single cycle 10 minutes at 72° C. Reaction products were electrophoresed on an agarose gel, excised and products purified from the gel into 40 µl sterile water using a Geneclean II kit according to the manufacturers instructions (Bio101, La Jolla, Calif., U.S.A.).

(d) Fourth amplification. One µl (500 pg) of 100 times diluted pCKV5 plasmid using 12.5 pmol of each of the primers MYCCKFOR (SEQ ID 05) and CKREV (SEQ ID 06) in a 50 µl reaction containing 0.25 mM dNTPs, 2.5 units Taqplus Precision DNA polymerase, and 1×PCR reaction buffer (Stratagene Inc, Amsterdam, Netherlands). The pCKV5 plasmid contains the human kappa constant reunion cDNA (McGregor D P, Molloy P E, Cunningham C, & Harris W J. 1994 Mol. Immunol. 31: 219-26) and the V5 epitope DNA (Southern J A, Young D F, Heaney F, Baumgartner W K, Randall R E. 1991 J. Gen. Virol. 72: 1551-7). The MYCCK-FOR primer anneals to the 5'-end of the kappa constant region DNA and appends the 3' part of the MYC epitope DNA. The CKREV primer anneals to the 3'-end of the kappa constant region DNA.

PCR reactions were carried out on a Eppendorf Master Cycler for 1 cycle of 2 minutes and 15 seconds at 94° C. followed by 30 cycles of 94° C., 45 seconds: 60° C., 45 seconds; 72° C., 2 minutes, followed by a single cycle 10 minutes at 72° C. Reaction products were electrophoresed on an agarose gel, excised and products purified from the gel into 40 μl sterile water using a Geneclean II kit according to the manufacturers instructions (Bio101, La Jolla, Calif., U.S.A.).

(e) Fifth amplification. One μl (500 pg) of 100 times diluted pCKV5 plasmid using 12.5 pmol of each of the primers MYCV5FOR (SEQ ID 07) and V5REV (SEQ ID 08) in a 50 μl reaction containing 0.25 mM dNTPs, 2.5 units Taqplus Precision DNA polymerase, and 1×PCR reaction buffer (Stratagene Inc, Amsterdam, Netherlands). The MYCV5FOR primer anneals to the 5'-end of the V5 epitope DNA and appends the 3' part of the MYC epitope DNA. The V5REV primer anneals to the 3'-end of the V5 epitope DNA.

PCR reactions were carried out on a Eppendorf Master Cycler for 1 cycle of 2 minutes and 15 seconds at 94° C. followed by 30 cycles of 94° C., 45 seconds; 60° C., 45 seconds; 72° C., 30 seconds, followed by a single cycle 10 minutes at 72° C. Reaction products were electrophoresed on an agarose gel, excised and products purified from the gel into 40 μl sterile water using a Geneclean II kit according to the manufacturers instructions (Bio101, La Jolla, Calif., U.S.A.).

(f) Sixth amplification. One μl (500 pg) of 100 times diluted pTACP2A plasmid (ref) using 12.5 pmol of each of the primers TAC3 (SEQ ID 09) and MYCTACREV (SEQ ID 10) in a 50 μl reaction containing 0.25 mM dNTPs, 2.5 units Taqplus Precision DNA polymerase, and 1×PCR reaction buffer (Stratagene Inc, Amsterdam, Netherlands). The TAC3 primer anneals to the 5'-end of the TAC promoter DNA. The MYCTACREV primer anneals to the 3'-end of the TAC promoter DNA and appends the 5' part of the MYC epitope DNA.

PCR reactions were carried out on a Eppendorf Master Cycler for 1 cycle of 2 minutes and 15 seconds at 94° C. followed by 30 cycles of 94° C., 45 seconds; 60° C., 45 seconds; 72° C., 30 seconds, followed by a single cycle 10 minutes at 72° C. Reaction products were electrophoresed on an agarose gel, excised and products purified from the gel into 40 μl sterile water using a Geneclean II kit according to the manufacturers instructions (Bio101, La Jolla, Calif., U.S.A.).

(g) First assembly PCR. One μl (50 ng) of each of the reaction products in (f) and (d) using 50 pmol of each of the primers TAC5 (SEQ ID 11) and CKREV (SEQ ID 06) in a 50 μl reaction containing 0.25 mM dNTPs, 2.5 units TaqDeep Vent DNA polymerase mixture (20:1), and 1×PCR reaction buffer (New England Biolabs, Beverly, Mass., U.S.A.). The TAC5 primer anneals to the 5'-end of the reaction product (f) and adds 20 nucleotides. The CKREV primer anneals to the 3'-end of the reaction product (d).

PCR reactions were carried out on a Eppendorf Master Cycler for 1 cycle of 2 minutes and 15 seconds at 94° C. followed by 30 cycles of 94° C. 45 seconds. 60° C. 45 seconds; 72° C. 45 seconds, followed by a single cycle 10 minutes at 72° C. Reaction products were electrophoresed on an agarose gel, excised and products purified from the gel into 40 μl sterile water using a Geneclean II kit according to the manufacturers instructions (Bio101, La Jolla, Calif., U.S.A.).

(h) Second assembly PCR. One μl (50 ng) of each of the reaction products in (f) and (e) using 50 pmol of each of the primers TAC5 (SEQ ID 11) and V5REV (SEQ ID 08) in a 50 μl reaction containing 0.25 mM dNTPs, 2.5 units TaqDeep Vent DNA polymerase mixture (20:1), and 1×PCR reaction buffer (New England Biolabs, Beverly, Mass., U.S.A.). The TAC5 primer anneals to the 5'-end of the reaction product (f) and adds 20 nucleotides. The V5REV primer anneals to the 3'-end of the reaction product (e).

PCR reactions were carried out on a Eppendorf Master Cycler for 1 cycle of 2 minutes and 15 seconds at 94° C. followed by 30 cycles of 94° C. 45 seconds; 60° C., 45 seconds; 72° C., 45 seconds, followed by a single cycle 10 minutes at 72° C. Reaction products were electrophoresed on an agarose gel, excised and products purified from the gel into 40 μl sterile water using a Geneclean II kit according to the manufacturers instructions (Bio101, La Jolla, Calif., U.S.A.).

(i) Third assembly PCR. One μl (50 ng) of each of the reaction products in (b) and (g) or using 50 pmol of each of the primers TAC3 (SEQ ID 09) and ORIREV (SEQ ID 02) in a 50 μl reaction containing 0.25 mM dNTPs, 2.5 units TaqDeep Vent DNA polymerase mixture (20:1), and 1×PCR reaction buffer (New England Biolabs, Beverly, Mass., U.S.A.). The TAC3 primer anneals 20 nucleotides downstream to the 5'-end of the reaction product (g) The ORIREV primer anneals to the 3'-end of the reaction product (b). The reaction product in (i) is called TAC-MYC-CK-REPA-CIS-ORI (SEQ ID 12).

PCR reactions were carried out on a Eppendorf Master Cycler for 1 cycle of 2 minutes and 15 seconds at 94° C. followed by 30 cycles of 94° C., 45 seconds; 60° C., 45 seconds; 72° C., 1 minute, followed by a single cycle 10 minutes at 72° C. Reaction products were electrophoresed on an agarose gel, excised and products purified from the gel into 40 μl sterile water using a Geneclean II kit according to the manufacturers instructions (Bio101, La Jolla, Calif., U.S.A.).

(j) Fourth assembly PCR. One μl (50 ng) of each of the reaction products in (b) and (h) or using 50 pmol of each of the primers TAC3 (SEQ ID 09) and ORIREV (SEQ ID 02) in a 50 μl reaction containing 0.25 mM dNTPs, 2.5 units TaqDeep Vent DNA polymerase mixture (20:1), and 1×PCR reaction buffer (New England Biolabs, Beverly, Mass., U.S.A.). The TAC3 primer anneals 20 nucleotides downstream to the 5'-end of the reaction product (g). The ORIREV primer anneals to the 3'-end of the reaction product (b). The reaction product in (i) is called TAC-MYC-V5-REPA-CIS-ORI (SEQ ID 13).

PCR reactions were carried out on a Eppendorf Master Cycler for 1 circle of 2 minutes and 15 seconds at 94° C. followed by 30 cycles of 94° C., 45 seconds; 60° C., 45 seconds; 72° C., 1 minute, followed by a single cycle 10 minutes at 72° C. Reaction products were electrophoresed on an agarose gel, excised and products purified from the gel into 40 μl sterile water using a Geneclean II kit according to the manufacturers instructions (Bio101, La Jolla, Calif., U.S.A.).

Preparation of in vitro transcription/translation reaction. The reaction was set up on ice, using a Promega bacterial linear template S30 coupled in vitro transcription/translation reaction kit as follows:

20 μl TAC-MYC-CK-REPA-CIS-ORI template (50 μg of final construct DNA SEQ ID 012 above); 20 μl TAC-MYC-V5-REPA-CIS-ORI template (0.5 μg of final construct DNA SEQ ID 013 above): 20 μl complete amino acid mix (Promega); 80 μl S30 Premix; 60 μl S30 mix, and the reaction was allowed to proceed at 25° C. for 30 minutes and placed on ice, then diluted 10 fold with blocking buffer (Superblock (Perbio Ltd), 0.1% Tween 20, 200 μg/ml herring sperm DNA).

Figure 5:
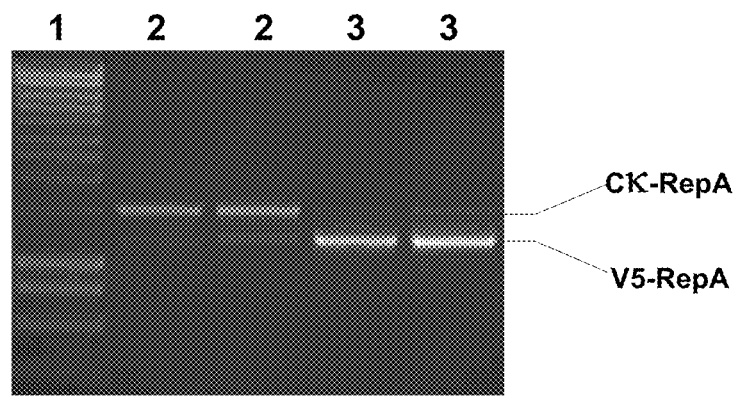
FIG. 5 demonstrates cis activity: 1:1 mixture of two different sized input DNAs (CK-RepA or V5-RepA) selected against either antibody. 1-Marker DNA; 2-PCR amplification after selection on anti-human CK antibody; 3-PCR amplification after selection on anti-V5 peptide antibody.

DNA-protein complex capture. NUNC star immunotubes were coated with 10 μg/ml of either anti-c-myc antibody, anti-V5 antibody, or anti-human kappa chain antibody, in 500 μl PBS per tube overnight at 4° C. An additional tube was left blank as a negative control. Tubes were washed 2×PBS and blocked for 1 hour at room temperature with Superblock/PBS/0.1 mg/ml herring sperm DNA/0.1% Tween 20 and then washed 2×PBS. 500 μl of diluted transcription/translation reaction was added to each tube and incubated at room temperature for 1 hour. Tubes were washed 5×PBS/0.1% Tween 20, then 1× 30 minutes with 2 ml Superblock/PBS/0.1 mg/ml herring sperm DNA/0.1% Tween 20. then 5×PBS. DNA was recovered with 300 μl T.E. buffer plus 300 μl phenol/chloroform for 5 minutes with shaking. This was centrifuged at 13,200 g for 5 minutes and DNA precipitated with 0.5 volume of 7.5M ammonium acetate, 20 μg glycogen and three volumes of absolute ethanol. Following centrifugation, pellets were washed with 70% ethanol, vacuum dried and resuspended in 20 μl water. 10 μl of recovered DNA was reamplified in 50 μl reactions with TAC3 (SEQ ID 09) and ORIREV (SEQ ID 02) primers. Reaction products were electrophoresed on a 1% agarose/TAE gel (FIG. 5).

EXAMPLE 2

Separating the RepA-DNA Complex

The two in vitro expression constructs (SEQID12 and SEQID13) already described in example 1 were used in a selection experiment against anti-human C-kappa antibody as described in Example 1, except that DNA was recovered and released from RepA by using either of following methods; Glycine, Triethylamine, Phenol/Chloroform, Proteinase K, and EDTA. These methods are described below.

Glycine: tube was incubated with 500 μl of 200 mM Glycine, 150 mM NaCl (pH2.0) for 10 minutes. The glycine eluate was then transferred to a fresh eppendorf tube and 50 μl of 2M Tris (pH 8.5) added.

Triethylamine: the tube was incubated 500 μl of 0.1M Triethylamine for 10 minutes and the triethylamine eluate was then transferred to a fresh eppendorf tube and 250 μl of 1M Tris (pH 7.4) added.

Phenol/Chloroform: as example 1 above.

Proteinase K: the tube was incubated with 500 μl of 100 mM Tris (pH 8.0), 10 mM EDTA (pH 8.0), 0.5% SDS for 30 minutes at 37° C. The Proteinase K eluate was then transferred to a fresh eppendorf tube.

EDTA: the tube was incubated with 250 μl of 10 mM Tris (pH 8.0), 1 mM EDTA 500 mM NaCl and 250 μl of Phenol/Chloroform for 5 minutes. The EDTA eluate was then transferred to a fresh eppendorf tube.

After recovery of DNA the DNA was Phenol/Chloroform extracted, where appropriate, followed by Ethanol precipitation as described in Example 1. 10 ul of resuspended DNA was reamplified in 50 ul reactions with TAC3 (SEQID09) and CISREV (SEQID019) primers. The CISREV primer anneals 196 bases upstream of the binding site of ORIREV (SEQID02). Reaction products were electrophoresed on a 1% agarose/TAE gel (data not shown). Only the CK-DNA containing construct (SEQID 12) was amplified, in approximately equivalent amounts.

This not only tells us that any of the methods described above for recovering and releasing DNA from RepA can be used, but this result also suggests that RepA interacts in a non-covalent manner with its cognate DNA.

EXAMPLE 3

Detection of Specific Anti-V5 Binders in a V5-spiking Experiment Using CIS Display Technology The in vitro expression constructs were prepared by adding the TAC promoter and either the V5 epitope or a 12-mer NNB library to the RepA-CIS-ORI region, by PCR amplification. Such constructs can be prepared by many methods known to one skilled in the art, for example, by amplifiying different fragments of DNA followed by assembly PCR. In this example, the initial amplification template was the R1 plasmid which contains the RepA-CIS-ORI region (Masai, H. and Arai, K.(1988). Nucleic Acids Res. 16, 6493-6514).

(a). Primary amplification. The RepA-CIS-ORI region was PCR amplified from a single colony of the strain ECO K12 harbouring plasmid R1 using 12.5 pmol of each of the primers REPAFOR (SEQ ID 01) and ORIREV408 (SEQ ID 20) in a 50 μl reaction containing 0.25 mM dNTPs, 2.5 units TaqDeep Vent DNA polymerase mixture (20:1), and 1×PCR reaction buffer (New England Biolabs, Beverly, Mass., U.S.A.). The REPAFOR primer anneals to the 5'-end of the RepA coding region. The ORIREV408 primer anneals to the downstream of the 3'-end of the non-coding ORI region.

PCR reactions were carried out on a Eppendorf Master Cycler for 1 cycle of 4 minutes and 30 seconds of 94° C. followed by 25 cycles of 94° C. 30 seconds; 60° C., 45 seconds; 72° C., 1 minute, followed by a single cycle 10 minutes at 72° C. Reaction products were electrophoresed on an agarose gel, excised and products purified from the gel into 40 μl sterile water using a Geneclean II kit according to the manufacturers instructions (Bio101, La Jolla, Calif., U.S.A.).

(b). Secondary amplification. One μl (500 pg) of 100 times diluted gel-purified primary reaction product was re-amplified using 12.5 pmol of each of the primers V5(NNB)REPFOR (SEQ ID 21) and ORIREV408 (SEQ ID 20) in a 50 μl reaction containing 0.25 mM dNTPs, 2.5 units TaqDeep Vent DNA polymerase mixture (20:1), and 1×PCR reaction buffer (New England Biolabs, Beverly, Mass., U.S.A.). The V5(NNB)REPFOR primer anneals to the 5'-end of the primary reaction product and appends the V5 epitope DNA. The ORIREV408 primer anneals to the 3'-end of the primary reaction product.

PCR reactions were carried out on a Eppendorf Master Cycler for 1 cycle of 4 minutes and 30 seconds of 94° C. followed by 25 Cycles of 94° C., 30 seconds; 60° C., 45 seconds; 72° C., 1 minute, followed by a single cycle 10 minutes at 72° C. Reaction products were electrophoresed on an agarose gel, excised and products purified from the gel into 40 μl sterile water using a Geneclean II kit according to the manufacturers instructions (Bio101, La Jolla, Calif., U.S.A.).

(c). Third amplification. One μl (500 pg) of 100 times diluted gel-purified primary reaction product was re-amplified using 12.5 pmol of each of the primers NNBREPFOR (SEQ ID 22) and ORIREV408 (SEQ ID 20) in a 50 μl reaction containing 0.25 mM dNTPs, 2.5 units TaqDeep Vent DNA polymerase mixture (20:1), and 1×PCR reaction buffer (New England Biolabs, Beverly, Mass., U.S.A.). The NNBREPFOR primer anneals to the 5'-end of the primary, reaction product and appends a random amino acid 12-mer NNB library DNA. The ORIREV408 primer anneals to the 3'-end of the primary reaction product.

PCR reactions were carried out on a Eppendorf Master Cycler for 1 cycle of 4 minutes and 30 seconds of 94° C. followed by, 25 cycles of 94° C. 30 seconds: 60° C., 45 seconds: 72° C. 1 minute, followed by a single cycle 10 minutes at 72° C. Reaction products were electrophoresed on an agarose gel, excised and products purified from the gel into 40 μl sterile water using a Geneclean II kit according to the manufacturers instructions (Bio101, La Jolla, Calif., U.S.A.).

(d). Fourth amplification. One μl (500 pg) of 100 times diluted pTACP2A plasmid (ref) using 12.5 pmol of each of the primers TACFARUP (SEQ ID 23) and TACREV (SEQ ID 27) in a 50 μl reaction containing 0.25 mM dNTPs, 2.5 units TaqDeep Vent DNA polymerase mixture (20:1), and 1×PCR reaction buffer (New England Biolabs, Beverly, Mass., U.S.A.). The TACFARUP primer anneals to the 5'-end of the TAC promoter DNA. The TACREV primer anneals to the 3'-end of the TAC promoter DNA.

PCR reactions were carried out on a Eppendorf Master Cycler for 1 cycle of 1 minutes and 45 seconds of 94° C. followed by 25 cycles of 94° C., 15 seconds; 60° C., 30 seconds; 72° C., 30 seconds, followed by a single cycle 10 minutes at 72° C. Reaction products were electrophoresed on an agarose gel, excised and products purified from the gel into 40 µl sterile water using a Geneclean II kit according to the manufacturers instructions (Bio101, La Jolla, Calif., U.S.A.).

(e). First assembly PCR. One µl (50 ng) of each of the reaction products in (b) and (d) using 50 pmol of each of the primers TACFARUP (SEQ ID 23) and ORIREV408 (SEQ ID 20) in a 50 µl reaction containing 0.2 mM dNTPs, 2.5 units TaqDeep Vent DNA polymerase mixture (20:1), and 1×PCR reaction buffer (New England Biolabs, Beverly, Mass., U.S.A.). The TACFARUP primer anneals to the 5'-end of the reaction product (d). The ORIREV480 primer anneals to the 3'-end of the reaction product (b). The reaction product in (e) is called TAC-V5-REPA-CIS-ORI-408 (SEQ ID 24).

PCR reactions were carried out on a Eppendorf Master Cycler for 1 cycle of 1 minutes and 45 seconds of 94° C. followed by 25 cycles of 94° C., 15 seconds; 60° C., 30 seconds; 72° C., 1 minute and 30 seconds, followed by a single cycle 10 minutes at 72° C. Reaction products were electrophoresed on an agarose gel, excised and products purified from the gel into 40 µl sterile water using a Geneclean II kit according to the manufacturers instructions (Bio101, La Jolla, Calif., U.S.A.).

(f). Second assembly PCR. One µL (50 ng) of each of the reaction products in (c) and (d) using 50 pmol of each of the primers TACFARUP (SEQ ID 23) and ORIREV408 (SEQ ID 20) in a 50 µl reaction containing 0.25 mM dNTPs. 2.5 units TaqDeepVent DNA polymerase mixture (20:1), and 1×PCR reaction buffer (New England Biolabs, Beverly, Mass., U.S.A.). The TACFARUP primer anneals to the 5'-end of the reaction product (d). The ORIREV480 primer anneals to the 3'-end of the reaction product (c).

PCR reactions were carried out on a Eppendorf Master Cycler for 1 cycle of 1 minutes and 45 seconds of 94° C. followed by 25 cycles of 94° C., 15 seconds; 60° C., 30 seconds; 72° C., 1 minute and 30 seconds, followed by a single cycle 10 minutes at 72° C. Reaction products were electrophoresed on an agarose gel, excised and products purified from the gel into 40 µl sterile water using a Geneclean II kit according to the manufacturers instructions (Bio101, La Jolla, Calif., U.S.A.). The reaction product in (f) is called TAC-NNB-REPA-CIS-ORI-408 (SEQ ID 25).

Preparation of in vitro transcription/translation reaction: The reaction set was set up on ice, using a Promega bacterial linear template S30 coupled in vitro transcription/translation reaction kit as follows:

20 µl of 5000 times diluted TAC-V5-REPA-CIS-ORI-408 template (0.1 ng of final construct DNASEQ ID 24 above)
20 µl of 5 TAC-NNB-REPA-CIS-ORI-408 template (0.5 µg of final construct DNASEQ ID 25 above)
20 µl complete amino acid mix (Promega)
80 µl S30 Premix
60 µl S30 mix and the reaction was allowed to proceed at 25° C. for 30 minutes and placed on ice, then diluted 10 fold with 2% Marvel/PBS.

DNA-protein complex capture. NUNC star immunotubes were coated with 10 µg/ml of anti-V5 antibody in 500 µl PBS overnight at 4° C. An additional tube was left blank as a negative control. Tubes were washed 2×PBS and blocked for 1 hour at room temperature with blocking buffer (2% Marvel, 0.1% Tween 20, 0.1 mg/ml herring sperm DNA) and then washed 2×PBS. 1 ml of diluted transcription/translation reaction was added to each tube and incubated at room temperature for 1 hour. Tubes were washed 5×PBS/0.1% Tween 20 and then 5×PBS. DNA was recovered with 500 µl TE buffer plus 500 µl phenol/chloroform. This was centrifuged at 13,200 g for 5 minutes and DNA precipitated with ⅒ volume of 3M sodium acetate, 50 µg/ml glycogen and two volumes of absolute ethanol. Following centrifugation, pellets were washed with 70% ethanol, vacuum dried and resuspended in 40 µl water. 20 µl of recovered DNA was reamplified in 50 µl reactions with the biotinylated primers bTAC6 (SEQ ID 26) and bCISREV (SEQ ID 19). Reaction products were electrophoresed on a 1% agarose/TAE gel.

Cloning of recovered DNA into the expression vector pDMG-K (SEQ ID 27). Reaction product were gelpurified and eluted with 50 µl sterile water using a QIAquick Gelextracation kit according to the manufacturers instructions (QIAGEN LtdWest Sussex, U.K.). Both the purified reaction product and the plasmid pDMG-K were digested with 20 units of NcoI and NotI (New England Biolabs, Beverly, Mass., U.S.A.). The cut plasmid was gelpurified using a QIAquick Gelextracation kit according to the manufacturers instructions (QIAGEN LtdWest Sussex, U.K.), then treated with 0.01 units of Calf Intestinal Alkaline Phosphatase (Promega, Southampton, U.K.) followed by phenol/chloroform extraction and ethanol precipitation as described above. Precipitated DNA was dissolved in 20 µl of water. The cut PCR product was transferred to Streptavidin coated strips (Roche Diagnostics Ltd, East Sussex, U.K.) in 1×TBS, 0.3 mg/ml BSA, 0.1% Tween 20 and incubated for 30 minutes at room temperature, shaking. This approach removes the flanking biotinylated DNA upstream and downstream of the NcoI and NotI site of the PCR product and enables recovery of the small DNA fragment containing the selected peptide sequence. Supernatant was phenol/chloroform extracted and ethanol precipitated as described above. Precipitated DNA was dissolved in 10 µl of water. Cut plasmid and the isloated small DNA fragment containing the selected peptide sequence, both having NcoI and NotI overhangs, were ligated using a Quick ligation kit according to the manufacturers instructions (New England Biolabs, Beverly, Mass., U.S.A.) followed by phenol/chloroform extraction and ethanol precipitation as described above. Precipitated DNA was dissolved in 10 µl of water and electroporated into electrocompetent TG1 cells according to the manufacturers instructions (Stratagene, U.S.A.) and selected on plates with 2×TY, 100 µg/ml ampicillin, and 2% glucose.

Figure 6:
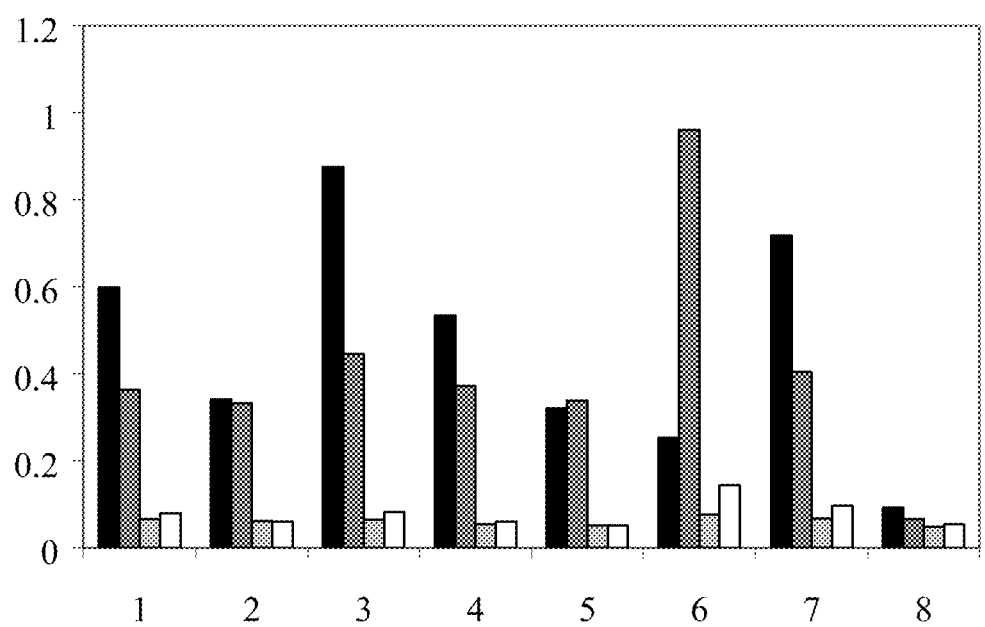
FIG. 6 shows the specificty of anti-V5 antibody binding clones. ELISA screening, read at 450 nM, of the seven clones (1-7) that shows specific binding to anti-V5 antibody. The bars in group of four represent the ELISA signal of the clones screened against from left to right; anti-human kappa region antibody, anti-V5 antibody, BSA, and blank. A negative control that neither express CK nor V5 is also presented (8).

Anti-V15 antibody ELISA screening of selected clones. 88 colonies were picked into 400 µl of 2×TY, 2% glucose, and 100 µg/ml ampicillin and grown overnight at 37° C., shaking 300 rpm. 50 µl of the overnight cultures were transferred into 1 ml of 2×TY, 2% glucose, and 100 µg/ml ampicillin and grown at 37° C., shaking 300 rpm until OD 0.5. Then the cells were centrifuged at 1000×g for 10 minutes. The supernatants were discarded and pellets were resuspended in 600 µl of 2×TY, 0.4M sucrose, 100 µg/ml ampicillin, and 1 mM IPTG and grown for 4 hours at 37° C. 300 rpm. After induction the cells were centrifuged at 1000×g for 10 minutes. 150 µl of the supernatants were used in the ELISA test. NUNC Maxisorp plates were coated with 100 µl of 1 µg/ml in 1×PBS of either anti-human kappa region antibody or anti-V5 antibody or 50 µg/ml of BSA for 7 hours at room temperature. An additional plate was left blank, only coated with PBS. Wells were rinsed 2×PBS followed by blocking for 1 hour at room temperature with 300 µl of 4% Marvel, 0.1% Tween in 1×PBS. Wells were rinsed 2×PBS, then 150 µl of supernatant and 150 µl of 4% Marvel, 0.1% Tween 20 in 1×PBS were added to wells and incubated for 1 hour at room temperature. Wells were then washed 2×PBS, 0.1% Tween 20 and 2×PBS. Secondary antibody anti-human kappa region antibody conjugated to horse radish peroxidase (HRP) (final concentration 1.6 μg/ml) was diluted 500 times in 4% Marvel, 0.1% Tween 20, 1× PBS and added to wells and incubated for 1 hour at room temperature. Wells were then washed 4×PBS, 0.1% Tween 20 and 2×PBS. The HRP signal was detected by adding 200 μl of TMB substrate. Reaction was stopped with 100 μl of 0.5M sulphuric acid. Absorbance was read at 450 nm. 35 out of 88 clones expressed well judged by HRP signal from clones screened against anti-human kappa region antibody. 7 out of these 35 clones showed specific binding to anti-V5 antibody, thereby enriching V5-peptides from 1 in 5000 to 1 in 5, i.e. an enrichment factor of 1000 (FIG. 6).

EXAMPLE 4

CIS Display Library Construction, Selection & Screening Against *Bacillus globigii*

Library Construction

To generate library DNA, a promoter library DNA fragment and the RepA-CIS-ori fragment must be generated, then linked together by digestion-ligation. The tac promoter from a P2A-HA vector was used in this example, but many available promoters could be used, and are well known to those skilled in the art. The initial PCR of Rep-CIS-ori and TAC fragments appends Bsp120I site and the random library/NotI site respectively. Two master mixes were prepared:

10 μl of 1:50 diluted P2A-HA plasmid DNA (25 ng/reaction) was PCR amplified in 20×50 μl reaction volume containing 200 μM dNTPs, 1×NEB polymerase amplification buffer (10 mM KCl, 10 mM (NH$_4$)$_2$SO$_4$; 20 mM Tris-HCl pH 8.8, 2 mM MgSO4, 0.1% TritonX-100) with 10 pmol of each of the primers TACFARUP (SEQ ID 23) and NTERM18MER (SEQ ID 28) primers and 2 units of 20:1 Taq DNA polymerase: Deep Vent DNA polymerase mixture (NEB) for 25 cycles of 94° C., 40 seconds; 60° C., 40 seconds; 72° C., 60 seconds; followed by a 5 minutes extension at 72° C. 20 μl of reaction product were electrophoresed on a 1% agarose/TAE gel and photographed, while the remainder was Qiagen column purified into 200 μl water.

10 μl of Bsp120I corrected Rep-CIS-ori DNA (50 ng/reaction) was PCR amplified in 10×50 μl reaction volume containing 200 mM dNTPs, 1×NEB polymerase amplification buffer (10 mM KCl, 10 mM (NH$_4$)$_2$SO$_4$, 20 mM Tris-HCl pH 8.8, 2 mM MgSO4, 0.1% TritonX-100) with 10 pmol of each of the primers BSPREPAFOR (SEQ ID 29) and ORIREV (SEQ ID 02) primers and 2 units of 20:1 Taq DNA polymerase: Deep Vent DNA polymerase mixture (NEB) for 30 cycles of 94° C., 40 seconds; 60° C., 40 seconds; 72° C., 90 seconds; followed by a 5 minutes extension at 72° C. 20 μl of reaction product were electrophoresed on a 1% agarose/TAE gel and photographed, while the remainder was Qiagen column purified into 120 μl water.

Library-TAC product was then digested with 10 μl NotI (NEB) (100 u) for 1 hour at 37° C. in a 300 μl reaction volume, then Qiagen column purified into a 120 μl volume of water. The two products were then joined by restriction-ligation as follows:

| | |
|---|---|
| 10× NEB buffer 4 | 17 μl |
| 100 mM ATP (SIGMA) | 15 μl |
| 10 mg/ml acetylated BSA (NEB) | 1 μl |

-continued

| | |
|---|---|
| RepA DNA | 40 μl |
| TAC-library DNA | 40 μl |
| Bsp120I (10 u/μl Fermentas) | 5 μl |
| NotI (10 u/μl NEB) | 5 μl |
| T4 DNA ligase (400 u/μl NEB) | 5 μl |
| Water | 39 μl |

Reaction was carried out at 37° C. for two hours. 20 μl was assessed by gel electrophoresis, 30 μl was PCR amplified directly in 10×50 μl reactions, and the remainder was gel purified and the library band excised, Qiagen column purified and PCR amplified in 20×50 μl reactions with primers TACFAR4 (SEQ ID 30) and ORIREV (SEQ ID 02) for 30 cycles of 94° C., 40 seconds; 60° C., 40 seconds; 72° C., 90 seconds; followed by a 5 minutes extension at 72° C. DNA was gel purified in 4 Qiagen columns and the 200 μl eluate pooled for ITT reactions/selection.

Round 1 Selection

2×200 μl ITT reaction was set up and incubated at room temperature for 1 hour as follows:

| | REACTION 1 |
|---|---|
| Library DNA | 56 μl (7 μg) |
| 2.5× buffer | 80 μl |
| 100 mM methionine | 2 μl |
| S30 extract | 60 μl |

1 ml of blocking buffer was added to each reaction (Block buffer is 4% Marvel, 100 g/ml sheared salmon sperm DNA, 0.1% Tween 20, 2.5 mg/ml heparin, in TBS), spun at 10,000 g for 2 minutes, transferred to a fresh tube, then placed on ice.

100 μl *Bacillus globigii* (Bg) spore suspension was washed twice with 1 ml TBS/0.1% Tween 20 and was resuspended in 100 μl of Block buffer. This was then added to the Block buffer and allowed to bind at room temperature for 1 hour whilst mixing.

The mix was then centrifuged at 16,100 g for 1 minute and the spore pellet was washed six times with 1 ml of TBS/0.1% Tween 20 by mixing with a pipette and vortexing prior to centrifugation. The pellet was finally washed in 1 ml TBS and the supernatant was discarded.

DNA was eluted by incubation of the spores in 120 μl 0.5M sodium acetate pH5.5 for 10 minutes on a mixer. The spores were centrifuged at 16,100 g for 1 minute and the supernatant was neutralised by the addition of 120 μl Tris pH8.0 and then phenol/CHCl3 extracted for 5 minutes at 16,100 g. DNA was precipitated with 20 μg carrier glycogen and two and a half volumes of ethanol. DNA was pelleted at 16,100 g for 20 minutes and the pellet washed three times with 0.75 ml 70% ethanol, centrifuging for 3 minutes at 16,100 g in between each wash, then air dried and re-suspended in 20 μl water.

10 μl recovered DNA was PCR amplified in 10×50 μl reaction with primers CISREV (SEQ ID 19) and TACFAR5 (SEQ ID 31) and 2 units of 20:1 Taq DNA polymerase: Deep Vent DNA polymerase mixture (NEB) for 30 cycles of 94° C., 40 seconds; 60° C., 40 seconds; 72° C., 90 seconds; followed by a 5 minutes extension at 72° C. The DNA was purified, ethanol precipitated and re-suspended in 10 μl water. 5 μl were further amplified by PCR using the conditions above but using the primers NOTRECREV2 (SEQ ID 32) and TAC- FAR5 (SEQ ID 31) for 10 cycles. The product was purified using a Qiagen PCR purification kit and eluted into 50 µl 5 mM Tris pH 8.0.

Restriction-Ligation

This was carried out in a 30 µl reaction for 1 hour at 37° C. to reattach RepA-CIS-ori DNA to recovered peptides for a further round of selection.

| | |
|---|---|
| 10× NEB buffer 4 | 3 µl |
| 100 mM ATP (SIGMA) | 1.5 µl |
| 10 mg/ml acetylated BSA (NEB) | 0.3 µl |
| RepA DNA | 2 µl |
| TAC-library DNA | 10 µl |
| Bsp120I (10 u/µl Fermentas) | 1.5 µl |
| NotI (10 u/µl NEB) | 1.5 µl |
| T4 DNA ligase (400 u/µl NEB) | 1.5 µl |
| Water | 8.7 µl |

20 µl was PCR amplified directly in 10×50 µl reactions with primers TACFAR5.1 (SEQ ID 33) and ORIREV (SEQ ID 02) for 20 cycles of 94° C., 40 seconds; 60° C. 40 seconds; 72° C., 90 seconds; followed by a 5 minutes extension at 72° C. DNA was gel purified in 1 Qiagen column and the eluate used for Round 2 of ITT reactions/selection (58 µl used in R2).

Round 2

Second round selection was carried out as for round 1, with the following changes: Approximately 3 µg of input DNA were used. Block buffer was 2% bovine serum albumin, 1% gelatin, 100 µg/ml sheared salmon sperm DNA, 2.5 mg/ml heparin, in TBS. 10 µl washed spores used in each selection. Recovery PCRs used TACFAR5.2 (SEQ ID 34) and NOTRECREV2 (SEQ ID 32) primers. Finally, pull through PCR used TACFAR5.2 (SEQ ID 34) and ORIREV (SEQ ID 02) primers for 10 cycles.

Round 3

Third round selection was carried out as for round 2, with the following changes: Approximately 2.5 µg of input DNA was used. Recovery PCRs used TACFAR6 (SEQ ID 35) and NOTRECREV2 (SEQ ID 32) primers. Finally, pull through PCR used TACFAR6 (SEQ ID 35) and ORIREV (SEQ ID 02) primers for 10 cycles.

Round 4

Round 4 was carried out as for round 3, except that approximately 2 µg of input DNA was used for the selection. Recovery PCRs used TAC3 (SEQ ID 09) and NOTRECREV2 (SEQ ID 32) primers. Finally, pull through PCR used TAC3 (SEQ ID 09) and ORIREV (SEQ ID 02) primers for 10 cycles.

Round 5

Round 5 was carried out as for round 4.

For cloning out as NcoI-NotI fragments, the stored the recovered DNA from round 5 was PCR amplified with biotinylated TAC6 (SEQ ID 26) primer and NOTRECREV2 (SEQ ID 32). Digestion with NotI was followed by purification using Qiagen PCR purification kit, digestion with NcoI followed by incubation in a plate coated with streptavidin. Following phenol/CHCl3 purification and ethanol precipitation, the digested DNA was then ligated into a similarly digested pVIII phagemid vector and transformed into ER2738 *E. coli*, then plated on 2% glucose, 2×TY, 100 µg/ml ampicillin plates and incubated o/n at 37° C.

Individual colonies were picked into 200 µl 2% glucose, 2×TY, 100 µg/ml ampicillin medium in 96 well plates, and grown at 37° C./200 rpm for 6 hours. 100 µl was transferred to a deep-well plate containing 100 µl 2% glucose, 2×TY, 100 µg/ml ampicillin plus 10 µl M13K07 helper phage/well and incubated for 1 hour without shaking at 37° C. 500 µl per well of 2×TY, 100 µg/ml ampicillin/25 µg/ml kanamycin/20 µM IPTG medium was added and incubation carried out o/n at 37° C./200 rpm.

ELISA Screening

Figure 7:
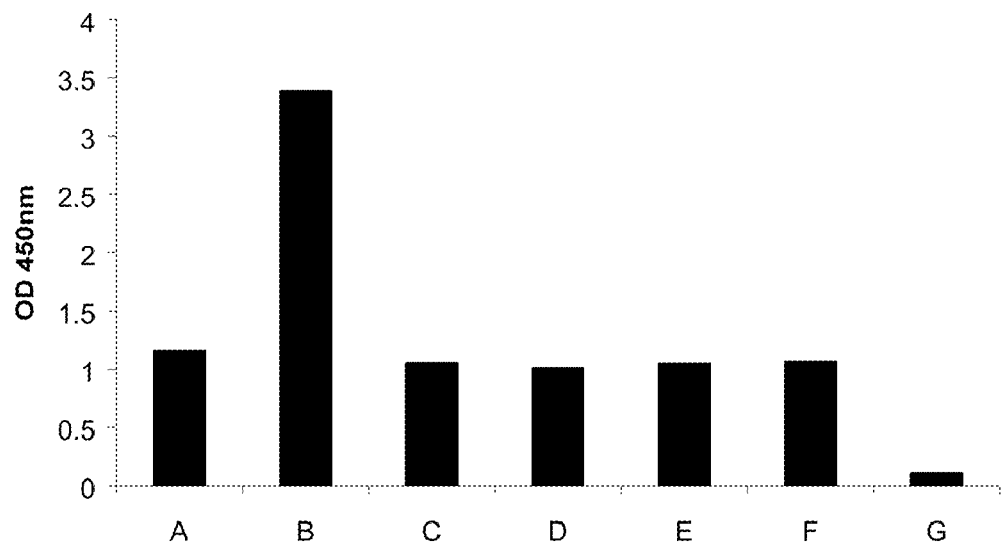
FIG. 7 shows culture supernatant ELISA OD 450 nm signals for peptides recovered after 5 rounds of selection against *B. globigii* spores in Example 4. A.=clone1e; B.=clone1f; C.=clone1g; D.=cloneSa; E.=clone10c; F.=clone10e; G.=negative control.

Round bottom 96 well plates were blocked with 4% Marvel in TBS/0.1% Tween 20 in PBS for 1 hour at room temperature. Picked phage cultures were centrifuged at 3000 g for 5 minutes and the phage supernatant was assayed in an ELISA. In each well 50 µl of phage supernatant were mixed with 5 µl Bg spores in 50 µl 4% bovine serum albumin, 1% gelatin in TBS and incubated whilst shaking at room temperature for 1 hour. The wells were washed 5× with 200 µl TBS/0.1% Tween20 by centrifugation at 3000 g for 5 minutes in between each wash before incubation with anti-M13 horseradish peroxidase conjugated antibody 0.2 µg/ml in 4% bovine serum albumin, 1% gelatin in TBS. The spores were incubated at room temperature for 1 hour whilst shaking. The wells were then washed 5× with TBS/0.1% Tween20 and the spores were transferred into a fresh plate. The spores were then washed once with TBS as described above before development with TMB substrate. The development was stopped with 0.5M $H_2SO_4$ and the solution was transferred to a flesh flat-bottomed plate for reading at 450 nm. Binding data for selected peptides is shown in FIG. 7.

EXAMPLE 5

CIS Display Library Construction, Selection & Screening Against Anti-V5 Antibody Library Construction was carried out as described in Example 4.

Round 1 Selection

1×200 µl in vitro transcription/translation reaction (ITT) reaction was set up and incubated at room temperature for 1 hour as described in Example 4. 1 ml of blocking buffer was added to each reaction (Block buffer is 5% skimmed milk powder, 100 µg/ml sheared salmon sperm DNA, 2.5 mg/ml heparin, in TBS), then placed on ice.

For the first round of library selection a 70×11 mm NUNC Maxisorp Immunotube (Life Technologies, Paisley, Scotland U.K.) was coated with 1 ml of 10 µg/ml of polyclonal anti-V5 peptide antibody (Harlan-Seralab) in PBS for 1 hour at 37° C. The tube was rinsed three times with PBS (fill & empty) and blocked with 3 ml block buffer for 1 hour at 37° C. and washed as before. Library protein-DNA complexes in block buffer were added, and incubated for 1 hour standing at room temperature. The tube was washed five times with PBS/0.1% Tween 20, then a further five times with PBS only.

DNA was eluted into 500 µl 1M Sodium acetate pH 5.2 for 10 minutes on the blood mixer, neutralized with 100 µl 1M Tris-HCl pH 8.0, then phenol/CHCl3 extracted for 5 minutes at 16,100 g. DNA was precipitated with 20 µg carrier glycogen, ½ volume 7.5M ammonium acetate, and three volumes of ethanol. DNA was pelleted at 16,100 g for 20 minutes and the pellet washed with 0.5 ml 70% ethanol for 5 minutes at 16,100 g then vacuum dried, and re-suspended in 20 µl water.

10 µl recovered DNA was PCR amplified in 1×50 µl reaction with primers NOT1RECREV2 (SEQ ID 32) and TACFAR4 (SEQ ID 30) and 2 units of 20:1 Taq DNA polymerase: Deep Vent DNA polymerase mixture (NEB) for 30 cycles of 94° C., 40 seconds; 60° C., 40 seconds; 72° C., 90 seconds; followed by a 5 minutes extension at 72° C. 50 µl of reaction product were electrophoresed on a 1% agarose/TAE gel and photographed, then GeneClean purified into 10 µl water. DNA was reattached to RepA DNA and reamplified for round two as described in example 4 using TACFAR5 (SEQ ID 31) and ORIREV (SEQ ID 02) primers.

Second round selection was carried out as for round 1, using the same primer pairs as described in example 4, with the following changes: Anti-V5 antibody coating concentration was reduced to 5 µg/ml. Input DNA was approximately 4 µg. Third round selection was carried out as for round 2, with the following changes: Approximately 4 µg of input DNA was used. Recovery PCRs used TACFAR5.1 (SEQ ID 33) and NOTRECREV2 (SEQ ID 32) primers. Finally, pull through PCR used TACFAR6 (SEQ ID 35) and ORIREV (SEQ ID 02) primers for 10 cycles. Round 4 was carried out as for round 3.

For cloning out as NcoI-NotI fragments, the stored the recovered DNA from round 4 the recovered DNA from round 4 was PCR amplified with biotinylated (SEQ ID 26) TAC6 and NOTREPRECREV9 (SEQ ID 32) primers and cloned into pVIII phagemid vector and electroporated into electrocompetent TG-1 *E. coli*, as described in example 4.

Individual colonies were picked into 200 µl 2% glucose. 2×TY. 100 µg/ml ampicillin medium in 96 well plates, and grown at 37° C./200 rpm for 6 hours. 100 µl was transferred to a deep-well plate containing 100 µl 2% glucose, 2×TY, 100 µg/ml ampicillin plus $10^9$ kru M13K07 helper phage/well and incubated for 1 hour without shaking at 37° C. 400 µl per well of 2×TY, 100 µg/ml ampicillin/25 µg/ml kanamycin/20 µM IPTG medium was added and phase amplification continued for 16 hours at 37° C. while shaking at 200 rpm. Bacterial cultures were spun in microtitre plate carriers at 2000 g for 10 minutes at 4° C. in a benchtop centrifuge to pellet bacteria and culture supernatant used for ELISA.

Figure 8:
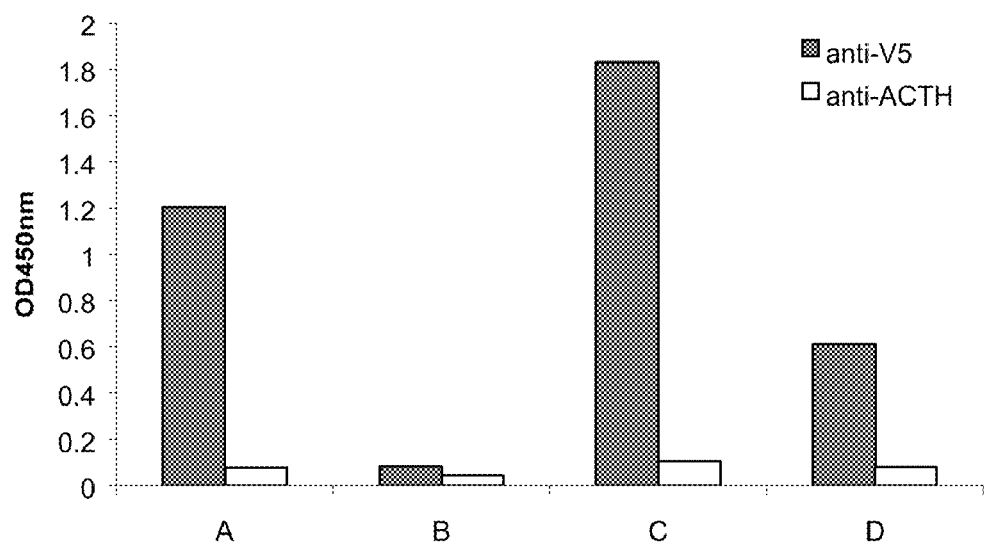
FIG. 8 shows OD 450 nm signals for peptides isolated after 4 rounds of selection against anti-V5 antibody in Example 5. A.=P1C12; B.=P2H1; C.=P1B5; D.=P2B8. Peptide-phage were tested against anti-V5 and anti-ACTH peptide antibodies.

A NUNC Maxisorp ELISA plate was coated with 100 ng/well anti-V5 peptide antibody in 100 µl/well PBS for one hour at 37° C. The plate was washed 2×200 µl/well PBS and blocked for 1 hour at 37° C. with 200 µl/well 2% BSA/PBS and then washed 2×200 µl/well PBS. 50 µl phage culture supernatant was added to each well containing 50 µl/well 4% BSA/PBS, and allowed to bind for 1 hour at room temperature. The plate was washed two times with 200 µl/well PBS/0.1% Tween 20, then two times with 200 µl/well PBS. Bound phage were detected with 100 µl/well, 1:5000 diluted anti-M13-HRP conjugate (Amersham-Pharmacia) in 2% BSA/PBS for 1 hour at room temperature and the plate washed four times as above. The plate was developed for 5 minutes at room temperature with 100 µl/well TMB (3,3',5,5'-Tetramethylbenzidine) substrate buffer. The reaction was stopped with 100 µl/well 0.5N $H_2SO_4$ and read at 450 nm. Phagemid DNA of ELISA positive clones were then sequenced with standard pUC forward and reverse sequencing primers. The amino acid sequence of these clones isolated is shown below. Four ELISA positive clones were grown in 10 ml culture volumes and phage particles precipitated with PEG-NaCl and re-suspended in 1 ml PBS and 50 µl retested in ELISA as described above. OD450 nm signals against anti-V5 and control anti-ACTH peptide antibody are shown in FIG. 8.

Peptide sequences isolated after selection:

```
P1C12
C G C P T M A A R V R P V L N S K H    (SEQ ID 36)

P2H1
M T T V P V L M I S V                   (SEQ ID 37)
```

-continued
```
P1B5
T L S T R H H N V I D R F N L R N F    (SEQ ID 38)

P2B8
S I R T L T G S T P A Q F D A T A D    (SEQ ID 39)
```

EXAMPLE 6

Selection of Ovalbumin Binding Peptides from a CIS Display Library

For any selection methodology it is important that the selected entities are capable of binding to the target selected against, independently of the carrier molecule associated with it during selection and screening. In this example, selected peptides are selected and synthesized to allow confirmation of target binding. Random 12 mer peptide library construction was carried out as described in Example 3. Four rounds of selection were carried out as described in example 4 with 100 µg/ml ovalbumin (SIGMA, Dorset, UK) coated onto immunotubes.

For cloning out as NcoI-NotI fragments, the recovered DNA from round 4 was PCR amplified with biotinylated TAC6 (SEQ ID 26) and NOTIREPRECREV2 (SEQ ID 32) primers and cloned into a pVIII phagemid vector and electroporated into electrocompetent TG-1 *E. coli*, as described in example 4.

Individual colonies were picked into 200 µl 2% glucose, 2×TY, 100 µg/ml ampicillin medium in 96 well plates, and grown at 37° C./200 rpm for 6 hours. 100 µl was transferred to a deep-well plate containing 100 µl 2% glucose, 2×TY, 100 µg/ml ampicillin plus $10^9$ kru M13K07 helper phage/well and incubated for 1 hour without shaking at 37° C. 400 µl per well of 2×TY, 100 µg/ml ampicillin/25 µg/ml kanamycin/20 µM IPTG medium was added and phase amplification continued for 16 hours at 37° C. while shaking at 200 rpm. Bacterial cultures were spun in microtitre plate carriers at 2000 g for 10 minutes at 4° C. in a benchtop centrifuge to pellet bacteria and culture supernatant used for ELISA.

A NUNC Maxisorp ELISA plate was coated with 100 µg/well ovalbumin in 100 µl/well PBS overnight at 4° C. The plate was washed 2×200 µl/well PBS and blocked for 1 hour at 37° C. With 200 µl/well 2% BSA/PBS and then washed 2×200 µl/well PBS. 50 µl phage culture supernatant was added to each well containing 50 µl/well 4% BSA/PBS, and allowed to bind for 1 hour at room temperature. The plate was washed two times with 200 µl/well PBS/0.1% Tween 20, then two times with 200 µl/well PBS. Bound phase were detected with 100 µl/well, 1:5000 diluted anti-M13-HRP conjugate (Amersham-Pharmacia) in 2% BSA/PBS for 1 hour at room temperature and the plate washed four times as above. The plate was developed for 5 minutes at room temperature with 100 µl/well TMB (3,3',5,5'-Tetramethylbenzidine) substrate buffer. The reaction was stopped with 100 µl/well 0.5N $H_2SO_4$ and read at 450 nm. Phagemid DNA of ELISA positive clones were then sequenced with M13REV primer. The amino acid sequence of these clones isolated is shown below.

```
C1     A N L W R I V L H G W W    (SEQ ID 40)

C4     V S F M L L G P H R H R    (SEQ ID 41)

C6     L V L H W L S L G S R      (SEQ ID 42)
```

-continued

| | | |
|---|---|---|
| C8 | S N Q V V L I L H L R P | (SEQ ID 43) |
| Control | A E S W L H Q S W I H L | (SEQ ID 44) |

Figure 9:
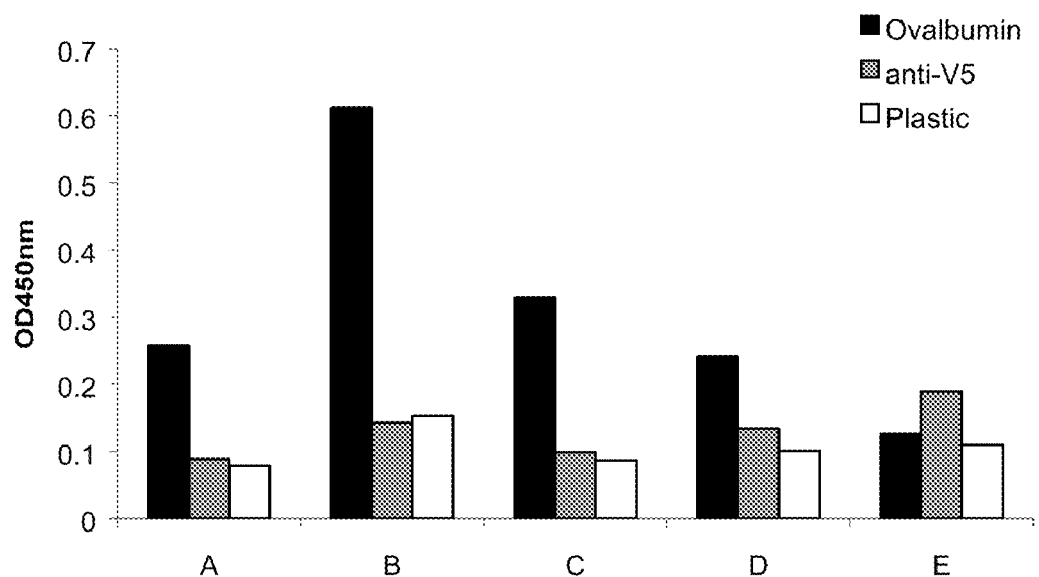
FIG. 9 shows OD 450 nm signals for synthetic peptides isolated after 4 rounds of selection against ovalbumin. A.=C1; B.=C4; C.=C6; D.=C8; E.=negative control. Peptides were tested against ovalbumin, anti-V5 antibody and blocked plate (plastic).

Peptide sequences from four representative ELISA positive clones were synthesized (SIGMA-Genosys Ltd) with biotin added to the C-terminus to aid detection in ELISA. These peptides were tested in ELISA against ovalbumin, along with a control peptide previously isolated by phage display selection against *B. globigii* spores. A NUNC Maxisorp ELISA plate was coated with 100 μg/well ovalbumin in 100 μl/well PBS, or, 200 ng/well ant-V5 polyclonal antibody in PBS, overnight at 4° C. The plate was washed 2×200 μl/well PBS and blocked for 1 hour at 37° C. with 200 μl/well 2% skimmed milk powder/PBS and then washed 2×200 μl/well PBS. 1 μg of diluted peptides were added to each well in 100 μl/well 2% BSA/PBS, and allowed to bind for 1 hour at room temperature. The plate was washed two times with 200 μl/well PBS/0.1% Tween 20, then two times with 200 μl/well PBS. Bound peptides were detected with 100 μl/well, 1:2000 diluted streptavidin-HRP conjugate (Pierce) in 2% BSA/PBS for 1 hour at room temperature and the plate washed four times as above. The plate was developed for 5 minutes at room temperature with 100 μl/well TMB (3,3',5,5'-Tetramethylbenzidine) substrate buffer. The reaction was stopped with 100 μl/well 0.5N $H_2SO_4$ and read at 450 nm (FIG. 9).

EXAMPLE 7

Display of Single-Chain Fv Antibody (scFv) Fragments in a CIS Display System

A tac-scFv-RepA-CIS-ori construct was constructed by PCR overlap extension essentially as described previously in example 1. Anti-mecoprop scFv DNA (Haptogen Ltd, Aberdeen, UK) was amplified in a 50 μl reaction volume containing 200 μM dNTPs, 1×NEB polymerase amplification buffer (10 mM KCl, 10 mM $(NH_4)_2SO_4$, 20 mM Tris-HCl pH 8.8, 2 mM MgSO4, 0.1% TritonX-100) with 10 pmol of each of the primers TACMECOFOR (SEQ ID 45) and REPAMECOBAK (SEQ ID 46) and 2 units of 20:1 Taq DNA polymerase: Deep Vent DNA polymerase mixture (NEB) for 30 cycles of 94° C., 40 seconds; 60° C., 40 seconds; 72° C., 80 seconds; followed by a 5 minutes extension at 72° C. Products were electrophoresed on a 1% agarose/TAE gel and purified with a Geneclean II kit into 20 μl water. This was assembled with RepA-CIS-ori DNA generated with ORIREV408 (SEQ ID 20) and MECOREPAFOR (SEQ ID 47), and Tac promoter DNA generated with TACFARUP (SEQ ID 23) and MECO-TACBAK (SEQ ID 48) in a 50 μl reaction volume containing 200 μM dNTPs, 1×NEB polymerase amplification buffer (10 mM KCl, 10 mM $(NH_4)_2SO_4$, 20 mM Tris-HCl pH 8.8, 2 mM MgSO4, 0.1% TritonX-100) with 10 pmol of each of the primers TAC3 (SEQ ID 09) and ORIREV (SEQ ID 02) and 2 units of 20:1 Taq DNA polymerase: Deep Vent DNA polymerase mixture (NEB) for 30 cycles of 94° C., 40 seconds; 60° C., 40 seconds; 72° C., 80 seconds; followed by a 5 minutes extension at 72° C. Products were electrophoresed on a 1% agarose/TAE gel and purified with a Geneclean II kit into 20 μl water.

DNA was reamplified in 10×50 μl reactions containing 200 μl dNTPs, 1×NEB polymerase amplification buffer (10 mM KCl, 10 mM $(NH_4)_2SO_4$, 20 mM Tris-HCl pH 8.8, 2 mM MgSO4, 0.1% TritonX-100) with 10 pmol of each of the primers TAC3 (SEQ ID 09) and ORIREV (SEQ ID 02) and 2 units of 20:1 Taq DNA polymerase: Deep Vent DNA polymerase mixture (NEB) for 30 cycles of 94° C., 40 seconds: 60° C. 40 seconds; 72° C. 80 seconds; followed by a 5 minutes extension at 72° C. Products were electrophoresed on a 1% agarose/TAE gel and purified with a Geneclean II kit into 100 μl water.

ScFvDNA was then translated in the following two reaction conditions:

| | REACTION | |
|---|---|---|
| | 1 | 2 |
| Tac-ScFv-RepA DNA | 28 μl (1 μg) | 28 μl (1 μg) |
| 2.5× buffer | 40 μl | 40 μl |
| 10 mM methionine | 1 μl | 1 μl |
| $H_2O$ | 1 μl | — |
| S30 extract | 30 μl | 30 μl |

Reactions were incubated at 30° C. for 30 minutes then 1 μl 0.25M ox-glutathione added to reaction 2 and incubation at 30° C. continued for a further 30 minutes. 1 ml of blocking buffer was added to each reaction (Block buffer is 1% gelatin, 100 μg/ml sheared salmon sperm DNA, 2.5 μg/ml heparin, in TBS), spun at 10,000 g for minutes, then placed on ice.

NUNC star immunotubes were coated with 0.5 ml 10 μg/ml BSA-mecoprop conjugate, or 10 μg/ml BSA in PBS for 1 hour at 37° C. Tubes were washed 2×PBS, then blocked for 1 hour at room temperature with 3 ml blocking buffer on a blood mixer, then tubes were washed 2×PBS.

0.5 ml of each diluted ITT was added to either a blocked BSA coated or BSA-mecoprop coated tube and incubated at room temperature for 1 hour. Tubes were washed 5×TBS/0.1% Tween 20, 5×TBS.

Bound DNA was eluted for 10 minutes at room temperature with 0.5 ml of 0.5M NaCl/10 mM Tris pH 8, 1 mM EDTA, then extracted with 0.5 mL phenol/chloroform and precipitated with 20 μg, carrier glycogen, ½ volume 7.5M ammonium acetate, and three volumes of ethanol. DNA was pelleted at 14,000 g for 20 minutes and the pellet washed with 0.5 ml 70% ethanol for 5 minutes at 14,000 g then vacuum dried, and re-suspended in 20 μl water.

Figure 10:
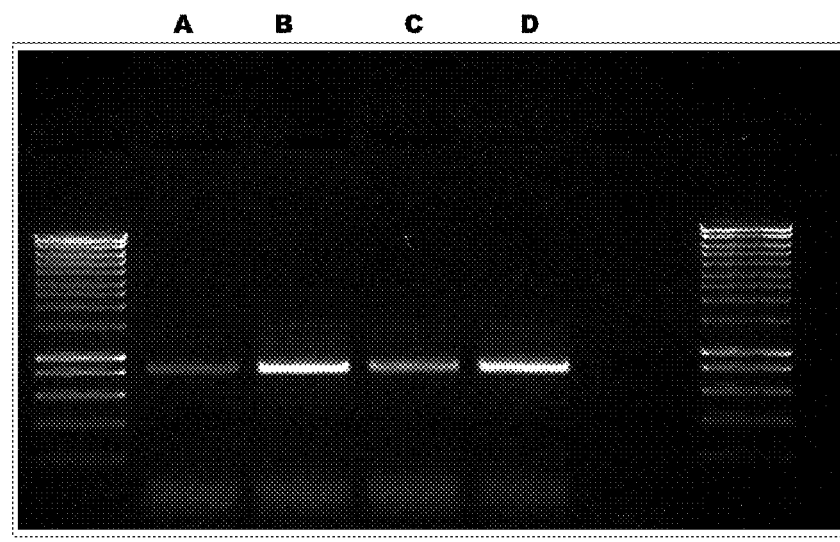
FIG. 10. shows PCR recoveries of scFv DNA after selection on BSA or BSA-mecoprop. A. Anti-mecoprop scFv selected on BSA, 2.5 mM ox-glutathione. B. Anti-mecoprop scFv selected on mecoprop-BSA, 2.5 mM ox-glutathione. C. Anti-mecoprop scFv selected on BSA, no ox-glutathione. D. Anti-mecoprop scFv selected on mecoprop-BSA, no ox-glutathione.

10 μl of recovered DNA was PCR amplified in a 50 μl reaction volume containing 200 μM dNTPs, 1×NEB polymerase amplification buffer (10 mM KCl, 10 mM $(NH_4)_2SO_4$, 20 mM Tris-HCl pH 8.8, 2 mM MgSO4, 0.1% TritonX-100) with 10 pmol of each of the primers TACMECOFOR (SEQ ID 45) and REPAMECOBAK (SEQ ID 46) and 2 units of 20:1 Taq DNA polymerase: Deep Vent DNA polymerase mixture (NTEB) for 30 cycles of 94° C., 40 seconds. 60° C., 40 seconds; 72° C., 80 seconds; followed by a 5 minutes extension at 72° C. Products were electrophoresed on a 1% agarose/TAE gel and photographed. Greater amounts of DNA were observed from selections on antibody target than with recovered from BSA coated tubes, indicating that functional scFv-RepA-DNA complexes were being selected (FIG. 10).

The invention claimed is:

1. A method for producing an in vitro peptide expression library comprising a plurality of peptides, wherein each peptide is non-covalently bound to the DNA construct encoding the peptide, comprising:
(a) providing a DNA construct comprising:
  (i) a DNA target sequence;
  (ii) DNA encoding a library member peptide; and
  (iii) DNA encoding a peptide capable of non-covalently binding to said DNA target sequence of (a)(i);
wherein said DNA construct and said peptide encoded by the DNA of (a) (iii) are selected to have cis-activity; and (b) expressing in an acellular environment a plurality of DNA constructs according to (a), wherein said DNA constructs encode a plurality of library member peptides such that each expressed peptide is non-covalently bound to the DNA from which it was produced.

2. The method according to claim 1 wherein said DNA construct further comprises:
(iv) a DNA element that directs cis-activity.

3. The method according to claim 2 wherein said DNA construct of (a) further comprises (v) DNA encoding a fragment comprising at least the C-terminal 20 amino acids of a repA protein; wherein said DNA element of (iv) is located 3' to said DNA of (ii), (iii) and (v).

4. The method according to claim 1 wherein the peptide encoded by said DNA of (iii) non-covalently binds directly to said DNA target sequence of (i).

5. The method according to claim 4 wherein the peptide encoded by said DNA of (iii) is a repA protein and wherein said DNA target sequence of (i) is an origin of replication that is recognized by a repA protein (ori).

6. The method according to claim 4 wherein said DNA of (ii) is bound to said DNA of (i) and (iii) by restriction enzyme digestion and ligation.

7. The method according to claim 3 wherein said repA is selected from the group consisting of repA of the IncI complex plasmids and repA of the IncF, IncB, IncK, IncZ and IncL/M plasmids.

8. The method according to claim 5 wherein said DNA construct comprises the sequence encoding repA, the cis DNA element and the ori DNA of the IncFII plasmid R1.

9. The method according to claim 3 wherein said repA protein comprises SEQ ID NO: 16 and wherein said cis DNA element comprises SEQ ID NO: 17.

10. The method according to claim 1 wherein DNA not bound by the peptide encoded by said DNA of (iii) is bound by a non-specific DNA binding protein.

11. The method according to claim 1 wherein said DNA is under the control of suitable promoter and translation sequences to allow for in vitro transcription and translation.

12. The method according to claim 1 wherein said library member peptide is an antibody or fragment thereof.

13. The method according to claim 1 wherein said library comprises at least $10^4$ molecules.

14. The method according to claim 1 wherein said expression is carried out in the presence of a compound that prevents nuclease activity, or reduces non-specific DNA-protein or protein-protein interactions.

15. The method according to claim 1, wherein said expression is carried out in acoupled bacterial transcription/translation extract system.

16. The method according to claim 15 wherein said coupled bacterial transcription/translation extract system is the S30 extract system.

17. A method of identifying and/or purifying a peptide exhibiting desired properties from an in vitro peptide expression library produced according to the method of claim 1, comprising at least the steps of (a) screening said library and (b) selecting and isolating the relevant library member.

18. A method of identifying a specific ligand binding peptide, said method comprising at least the steps of (a) screening an in vitro peptide expression library produced according to the method of claim 1 with ligand molecules which are optionally bound to a solid support; (b) selecting and isolating a library member binding to said ligand molecule; and (c) isolating the peptide which binds specifically to said ligand molecule.

19. The method according to claim 17 wherein said library member peptides are antibodies or fragments thereof.

20. The method of identifying and/or purifying a peptide having the ability to bind a specific DNA target sequence comprising at least the steps of
(a) providing an in vitro expression library according to claim 1 wherein the peptide encoded by the DNA of (iii) is a library member peptide having DNA binding activity and wherein said DNA target sequence of (i) is the target sequence of interest;
(b) selecting and isolating a library member in which the encoded peptide binds to said target sequence; and
(c) isolating the peptide which binds to said target sequence.

21. The method according to claim 20 wherein said library member peptides are zinc finger proteins, helix-loop-helix proteins or helix-turn-helix proteins.

22. The method according to claim 17 wherein said screening and/or selecting step is carried out in the presence of a compound that prevents nuclease activity or reduces non-specific DNA-protein or protein-protein interactions.

23. The method according to claim 22 wherein said compound is heparin.

24. The method according to claim 17 wherein additionally the DNA expressing said isolated peptide is isolated.

25. The method according to claim 24 further comprising cloning said DNA into an expression vector.

26. The method according to claim 25 further comprising introducing said expression vector into a cell in vitro.

27. The method according to claim 25 further comprising expressing the peptide encoded by said DNA.

28. An in vitro peptide expression library produced according to the method of claim 1.

29. A DNA construct as described in claim 1.

30. The method according to claim 18 wherein said library member peptides are antibodies or fragments thereof.

31. The method according to claim 18 wherein said screening and/or selecting step is carried out in the presence of a compound that prevents nuclease activity or reduces non-specific DNA-protein or protein-protein interactions.

32. The method according to claim 20 wherein said screening and/or selecting step is carried out in the presence of a compound that prevents nuclease activity or reduces non-specific DNA-protein or protein-protein interactions.

33. The method according to claim 18 wherein additionally the DNA expressing said isolated peptide is isolated.

34. The method according to claim 20 wherein additionally the DNA expressing said isolated peptide is isolated.

\* \* \* \* \*

SEQUENCE LISTING

<160> NUMBER OF SEQ ID NOS: 48

<210> SEQ ID NO 1
<211> LENGTH: 23
<212> TYPE: DNA
<213> ORGANISM: Artificial sequence
<220> FEATURE:
<223> OTHER INFORMATION: Primer

<400> SEQUENCE: 1
actgatcttc accaaacgta tta                                           23

<210> SEQ ID NO 2
<211> LENGTH: 22
<212> TYPE: DNA
<213> ORGANISM: Artificial sequence
<220> FEATURE:
<223> OTHER INFORMATION: Primer

<400> SEQUENCE: 2
tgcatatctg tctgtccaca gg                                            22

<210> SEQ ID NO 3
<211> LENGTH: 48
<212> TYPE: DNA
<213> ORGANISM: Artificial sequence
<220> FEATURE:
<223> OTHER INFORMATION: Primer

<400> SEQUENCE: 3
gagcttcaac aggggagggg gaggaggatc aactgatctt caccaaac                48

<210> SEQ ID NO 4
<211> LENGTH: 50
<212> TYPE: DNA
<213> ORGANISM: Artificial sequence
<220> FEATURE:
<223> OTHER INFORMATION: Primer

<400> SEQUENCE: 4
ctaggactgg attcaacggg gggaggagga tcaactgatc ttcaccaaac              50

<210> SEQ ID NO 5
<211> LENGTH: 49
<212> TYPE: DNA
<213> ORGANISM: Artificial sequence
<220> FEATURE:
<223> OTHER INFORMATION: Primer

<400> SEQUENCE: 5
cagaagagga tctgaatggg ggaggagggt ccactgtggc tgcaccatc               49

<210> SEQ ID NO 6
<211> LENGTH: 22
<212> TYPE: DNA
<213> ORGANISM: Artificial sequence
<220> FEATURE:
<223> OTHER INFORMATION: Primer

<400> SEQUENCE: 6
tcccctgttg aagctctttg tg                                            22

<210> SEQ ID NO 7
<211> LENGTH: 40

```
<212> TYPE: DNA
<213> ORGANISM: Artificial sequence
<220> FEATURE:
<223> OTHER INFORMATION: Primer

<400> SEQUENCE: 7
cagaagagga tctgaatggg ggaggagggt ccggaaaacc                         40

<210> SEQ ID NO 8
<211> LENGTH: 27
<212> TYPE: DNA
<213> ORGANISM: Artificial sequence
<220> FEATURE:
<223> OTHER INFORMATION: Primer

<400> SEQUENCE: 8
gctacgttga atccagtcct aggagag                                       27

<210> SEQ ID NO 9
<211> LENGTH: 22
<212> TYPE: DNA
<213> ORGANISM: Artificial sequence
<220> FEATURE:
<223> OTHER INFORMATION: Primer

<400> SEQUENCE: 9
catattgtcg ttagaacgcg gc                                            22

<210> SEQ ID NO 10
<211> LENGTH: 58
<212> TYPE: DNA
<213> ORGANISM: Artificial sequence
<220> FEATURE:
<223> OTHER INFORMATION: Primer

<400> SEQUENCE: 10
attcagatcc tcttctgaga tgagttttg ttcctcgagc atggtagatc ctgtttcc      58

<210> SEQ ID NO 11
<211> LENGTH: 42
<212> TYPE: DNA
<213> ORGANISM: Artificial sequence
<220> FEATURE:
<223> OTHER INFORMATION: Primer

<400> SEQUENCE: 11
cgatacctag cgttcggatc catattgtcg ttagaacgcg gc                      42

<210> SEQ ID NO 12
<211> LENGTH: 1788
<212> TYPE: DNA
<213> ORGANISM: Artificial sequence
<220> FEATURE:
<223> OTHER INFORMATION: DNA construct

<400> SEQUENCE: 12
catattgtcg ttagaacgcg gctacaatta atacataacc ttatgtatca tacacatacg    60
atttaggtga cactatagaa tacaagctta ctccccatcc ccctgttgac aattaatcat   120
ggctcgtata atgtgtggaa ttgtgagcgg ataacaattt cacacaggaa acaggatcta   180
ccatgctcga ggaacaaaaa ctcatctcag aagaggatct gaatgggga ggagggtcca   240 ctgtggctgc accatctgtc ttcatcttcc cgccatctga tgagcagttg aaatctggaa   300
ctgcctctgt tgtgtgcctg ctgaataact tctatcccag agaggccaaa gtacagtgga   360
```

| | | | | |
|---|---|---|---|---|
| aggtggataa | cgccctccaa | tcgggtaact | cccaggagag tgtcacagag | caggacagca | 420 |
| aggacagcac | ctacagcctc | agcaacaccc | tgacgctgag caaagcagac | tacgagaaac | 480 |
| acaaagtcta | cgcctgcgaa | gtcacccatc | agggcctgag ctcgcccgtc | acaaagagct | 540 |
| tcaacagggg | aggggagga | ggatcaactg | atcttcacca aacgtattac | cgccaggtaa | 600 |
| agaacccgaa | tccggtgttc | actcccgtg | aaggtgccgg aacgccgaag | ttccgcgaaa | 660 |
| aaccgatgga | aaaggcggtg | ggcctcacct | cccgttttga tttcgccatt | catgtggcgc | 720 |
| atgcccgttc | ccgtggtctg | cgtcggcgca | tgccaccggt gctgcgtcga | cgggctattg | 780 |
| atgcgctgct | gcaggggctg | tgtttccact | atgacccgct ggccaaccgc | gtccagtgtt | 840 |
| ccatcaccac | actggccatt | gagtgcggac | tggcgacaga gtccggtgca | ggaaaactct | 900 |
| ccatcacccg | tgccacccgg | gccctgacgt | tcctgtcaga gctgggactg | attacctacc | 960 |
| agacggaata | tgacccgctt | atcgggtgct | acattccgac cgacatcacg | ttcacactgg | 1020 |
| ctctgttgc | tgcccttgat | gtgtctgagg | atgcagtggc agctgcgcgc | cgcagtcgtg | 1080 |
| ttgaatggga | aaacaaacag | cgcaaaaagc | aggggctgga taccctgggt | atggatgagc | 1140 |
| tgatagcgaa | agcctggcgt | tttgtgcgtg | agcgtttccg cagttaccag | acagagcttc | 1200 |
| agtcccgtgg | aataaaacgt | gcccgtgcgc | gtcgtgatgc gaacagagaa | cgtcaggata | 1260 |
| tcgtcaccct | agtgaaacgg | cagctgacgc | gtgaaatctc ggaaggacgc | ttcactgcta | 1320 |
| atggtgaggc | ggtaaaacgc | gaagtggagc | gtcgtgtgaa ggagcgcatg | attctgtcac | 1380 |
| gtaaccgcaa | ttacagccgg | ctggccacag | cttctccctg aaagtgatct | cctcagaata | 1440 |
| atccggcctg | cgccggaggc | atccgcacgc | ctgaagcccg ccgtgcaca | aaaaaacagc | 1500 |
| gtcgcatgca | aaaacaatc | tcatcatcca | ccttctggag catccgattc | ccctgttttt | 1560 |
| taatacaaaa | tacgcctcag | cgacggggaa | ttttgcttat ccacatttaa | ctgcaaggga | 1620 |
| cttcccata | aggttacaac | cgttcatgtc | ataaagcgcc agccgccagt | cttacagggt | 1680 |
| gcaatgtatc | tttttaaacac | ctgtttatat | ctcctttaaa ctacttaatt | acattcattt | 1740 |
| aaaaagaaaa | cctattcact | gcctgtcctg | tggacagaca gatatgca | | 1788 |

<210> SEQ ID NO 13
<211> LENGTH: 1518
<212> TYPE: DNA
<213> ORGANISM: Artificial sequence
<220> FEATURE:
<223> OTHER INFORMATION: DNA construct

<400> SEQUENCE: 13

| | | | | |
|---|---|---|---|---|
| catattgtcg | ttagaacgcg | gctacaatta | atacataacc ttatgtatca | tacacatacg | 60 |
| atttaggtga | cactatagaa | tacaagctta | ctccccatcc ccctgttgac | aattaatcat | 120 |
| ggctcgtata | atgtgtggaa | ttgtgagcgg | ataacaattt cacacaggaa | acaggatcta | 180 |
| ccatgctcga | ggaacaaaaa | ctcatctcag | aagaggatct gaatggggga | ggagggtccg | 240 |
| gaaaacctat | cccaaaccct | ctcctaggac | tggattcaac ggggggagga | ggatcaactg | 300 |
| atcttcacca | aacgtattac | cgccaggtaa | agaacccgaa tccggtgttc | actcccgtg | 360 |
| aaggtgccgg | aacgccgaag | ttccgcgaaa | aaccgatgga aaaggcggtg | ggcctcacct | 420 |
| cccgttttga | tttcgccatt | catgtggcgc | atgcccgttc ccgtggtctg | cgtcggcgca | 480 |
| tgccaccggt | gctgcgtcga | cgggctattg | atgcgctgct gcaggggctg | tgtttccact | 540 |
| atgacccgct | ggccaaccgc | gtccagtgtt | ccatcaccac actggccatt | gagtgcggac | 600 |
| tggcgacaga | gtccggtgca | ggaaaactct | ccatcacccg tgccacccgg | gccctgacgt | 660 |

-continued

```
tcctgtcaga gctgggactg attacctacc agacggaata tgacccgctt atcgggtgct    720
acattccgac cgacatcacg ttcacactgg ctctgtttgc tgcccttgat gtgtctgagg    780
atgcagtggc agctgcgcgc cgcagtcgtg ttgaatggga aaacaaacag cgcaaaaagc    840
aggggctgga taccctgggt atggatgagc tgatagcgaa agcctggcgt tttgtgcgtg    900
agcgtttccg cagttaccag acagagcttc agtcccgtgg aataaaacgt gcccgtgcgc    960
gtcgtgatgc gaacagagaa cgtcaggata tcgtcaccct agtgaaacgg cagctgacgc   1020
gtgaaatctc ggaaggacgc ttcactgcta atggtgaggc ggtaaaacgc gaagtgagc    1080 gtcgtgtgaa ggagcgcatg attctgtcac gtaaccgcaa ttacagccgg ctggccacag   1140
cttctccctg aaagtgatct cctcagaata atccggcctg cgccggaggc atccgcacgc   1200
ctgaagcccg ccggtgcaca aaaaaacagc gtcgcatgca aaaacaatc tcatcatcca    1260 ccttctggag catccgattc cccctgtttt aatacaaaa tacgcctcag cgacggggaa    1320
ttttgcttat ccacatttaa ctgcaaggga cttccccata aggttacaac cgttcatgtc   1380
ataaagcgcc agccgccagt cttacagggt gcaatgtatc ttttaaacac ctgtttatat   1440
ctcctttaaa ctacttaatt acattcattt aaaaagaaaa cctattcact gcctgtcctg   1500
tggacagaca gatatgca                                                  1518
```

```
<210> SEQ ID NO 14
<211> LENGTH: 38
<212> TYPE: DNA
<213> ORGANISM: Artificial sequence
<220> FEATURE:
<223> OTHER INFORMATION: Estrogen Receptor Target Recognition Sequence

<400> SEQUENCE: 14
tcaggtcaga gtgacctgag ctaaaataac acattcag                              38

<210> SEQ ID NO 15
<211> LENGTH: 828
<212> TYPE: DNA
<213> ORGANISM: Artificial sequence
<220> FEATURE:
<223> OTHER INFORMATION: repA sequence
<220> FEATURE:
<221> NAME/KEY: CDS
<222> LOCATION: (1)..(828)
<223> OTHER INFORMATION:

<400> SEQUENCE: 15 atg gta aag aac ccg aat ccg gtg ttc act ccc cgt gaa ggt gcc gga       48
Met Val Lys Asn Pro Asn Pro Val Phe Thr Pro Arg Glu Gly Ala Gly
1               5                   10                  15 acg ccg aag ttc cgc gaa aaa ccg atg gaa aag gcg gtg ggc ctc acc       96
Thr Pro Lys Phe Arg Glu Lys Pro Met Glu Lys Ala Val Gly Leu Thr
            20                  25                  30 tcc cgt ttt gat ttc gcc att cat gtg gcg cat gcc cgt tcc cgt ggt      144
Ser Arg Phe Asp Phe Ala Ile His Val Ala His Ala Arg Ser Arg Gly
        35                  40                  45 ctg cgt cgg cgc atg cca ccg gtg ctg cgt cga cgg gct att gat gcg      192
Leu Arg Arg Arg Met Pro Pro Val Leu Arg Arg Arg Ala Ile Asp Ala
    50                  55                  60 ctg ctg cag ggg ctg tgt ttc cac tat gac ccg ctg gcc aac cgc gtc      240
Leu Leu Gln Gly Leu Cys Phe His Tyr Asp Pro Leu Ala Asn Arg Val
65                  70                  75                  80 cag tgt tcc atc acc aca ctg gcc att gag tgc gga ctg gcg aca gag      288
Gln Cys Ser Ile Thr Thr Leu Ala Ile Glu Cys Gly Leu Ala Thr Glu
```

```
                   85                   90                   95
tcc ggt gca gga aaa ctc tcc atc acc cgt gcc acc cgg gcc ctg acg      336
Ser Gly Ala Gly Lys Leu Ser Ile Thr Arg Ala Thr Arg Ala Leu Thr
            100                 105                 110 ttc ctg tca gag ctg gga ctg att acc tac cag acg gaa tat gac ccg      384
Phe Leu Ser Glu Leu Gly Leu Ile Thr Tyr Gln Thr Glu Tyr Asp Pro
        115                 120                 125 ctt atc ggg tgc tac att ccg acc gac atc acg ttc aca ctg gct ctg      432
Leu Ile Gly Cys Tyr Ile Pro Thr Asp Ile Thr Phe Thr Leu Ala Leu
    130                 135                 140 ttt gct gcc ctt gat gtg tct gag gat gca gtg gca gct gcg cgc cgc      480
Phe Ala Ala Leu Asp Val Ser Glu Asp Ala Val Ala Ala Arg Arg
145                 150                 155                 160 agt cgt gtt gaa tgg gaa aac aaa cag cgc aaa aag cag ggg ctg gat      528
Ser Arg Val Glu Trp Glu Asn Lys Gln Arg Lys Lys Gln Gly Leu Asp
                165                 170                 175 acc ctg ggt atg gat gag ctg ata gcg aaa gcc tgg cgt ttt gtg cgt      576
Thr Leu Gly Met Asp Glu Leu Ile Ala Lys Ala Trp Arg Phe Val Arg
            180                 185                 190 gag cgt ttc cgc agt tac cag aca gag ctt cag tcc cgt gga ata aaa      624
Glu Arg Phe Arg Ser Tyr Gln Thr Glu Leu Gln Ser Arg Gly Ile Lys
        195                 200                 205 cgt gcc cgt gcg cgt cgt gat gcg aac aga gaa cgt cag gat atc gtc      672
Arg Ala Arg Ala Arg Arg Asp Ala Asn Arg Glu Arg Gln Asp Ile Val
    210                 215                 220 acc cta gtg aaa cgg cag ctg acg cgt gaa atc tcg gaa gga cgc ttc      720
Thr Leu Val Lys Arg Gln Leu Thr Arg Glu Ile Ser Glu Gly Arg Phe
225                 230                 235                 240 act gct aat ggt gag gcg gta aaa cgc gaa gtg gag cgt cgt gtg aag      768
Thr Ala Asn Gly Glu Ala Val Lys Arg Glu Val Glu Arg Arg Val Lys
                245                 250                 255 gag cgc atg att ctg tca cgt aac cgc aat tac agc cgg ctg gcc aca      816
Glu Arg Met Ile Leu Ser Arg Asn Arg Asn Tyr Ser Arg Leu Ala Thr
            260                 265                 270 gct tct ccc tga                                                      828
Ala Ser Pro
        275

<210> SEQ ID NO 16
<211> LENGTH: 275
<212> TYPE: PRT
<213> ORGANISM: Artificial sequence
<220> FEATURE:
<223> OTHER INFORMATION: repA sequence

<400> SEQUENCE: 16

Met Val Lys Asn Pro Asn Pro Val Phe Thr Pro Arg Glu Gly Ala Gly
1               5                   10                  15

Thr Pro Lys Phe Arg Glu Lys Pro Met Glu Lys Ala Val Gly Leu Thr
            20                  25                  30

Ser Arg Phe Asp Phe Ala Ile His Val Ala His Ala Arg Ser Arg Gly
        35                  40                  45

Leu Arg Arg Arg Met Pro Pro Val Leu Arg Arg Ala Ile Asp Ala
    50                  55                  60

Leu Leu Gln Gly Leu Cys Phe His Tyr Asp Pro Leu Ala Asn Arg Val
65                  70                  75                  80

Gln Cys Ser Ile Thr Thr Leu Ala Ile Glu Cys Gly Leu Ala Thr Glu
                85                  90                  95

Ser Gly Ala Gly Lys Leu Ser Ile Thr Arg Ala Thr Arg Ala Leu Thr
```

-continued

```
                         100                 105                 110
Phe Leu Ser Glu Leu Gly Leu Ile Thr Tyr Gln Thr Glu Tyr Asp Pro
            115                 120                 125
Leu Ile Gly Cys Tyr Ile Pro Thr Asp Ile Thr Phe Thr Leu Ala Leu
        130                 135                 140
Phe Ala Ala Leu Asp Val Ser Glu Asp Ala Val Ala Ala Arg Arg
145                 150                 155                 160
Ser Arg Val Glu Trp Glu Asn Lys Gln Arg Lys Gln Gly Leu Asp
                165                 170                 175
Thr Leu Gly Met Asp Glu Leu Ile Ala Lys Ala Trp Arg Phe Val Arg
            180                 185                 190
Glu Arg Phe Arg Ser Tyr Gln Thr Glu Leu Gln Ser Arg Gly Ile Lys
        195                 200                 205
Arg Ala Arg Ala Arg Arg Asp Ala Asn Arg Glu Arg Gln Asp Ile Val
    210                 215                 220
Thr Leu Val Lys Arg Gln Leu Thr Arg Glu Ile Ser Glu Gly Arg Phe
225                 230                 235                 240
Thr Ala Asn Gly Glu Ala Val Lys Arg Glu Val Glu Arg Arg Val Lys
                245                 250                 255
Glu Arg Met Ile Leu Ser Arg Asn Arg Asn Tyr Ser Arg Leu Ala Thr
            260                 265                 270
Ala Ser Pro
        275

<210> SEQ ID NO 17
<211> LENGTH: 172
<212> TYPE: DNA
<213> ORGANISM: Artificial sequence
<220> FEATURE:
<223> OTHER INFORMATION: CIS DNA element

<400> SEQUENCE: 17
aagtgatctc ctcagaataa tccggcctgc gccggaggca tccgcacgcc tgaagcccgc    60
cggtgcacaa aaaacagcg tcgcatgcaa aaaacaatct catcatccac cttctggagc   120
atccgattcc ccctgttttt aatacaaaat acgcctcagc gacggggaat tt          172

<210> SEQ ID NO 18
<211> LENGTH: 195
<212> TYPE: DNA
<213> ORGANISM: Artificial sequence
<220> FEATURE:
<223> OTHER INFORMATION: ori sequence

<400> SEQUENCE: 18
tgcttatcca catttaactg caagggactt ccccataagg ttacaaccgt tcatgtcata    60
aagcgccagc cgccagtctt acagggtgca atgtatcttt taaacacctg tttatatctc   120
ctttaaacta cttaattaca ttcatttaaa aagaaaacct attcactgcc tgtcctgtgg   180
acagacagat atgca                                                    195

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
```
aattccccgt cgctgaggcg                                                    20

<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
cgtaagccgg tactgattga                                                    20

<210> SEQ ID NO 21
<211> LENGTH: 110
<212> TYPE: DNA
<213> ORGANISM: Artificial sequence
<220> FEATURE:
<223> OTHER INFORMATION: Primer

<400> SEQUENCE: 21
cacaggaaac aggatctacc atggccggaa aacctatccc aaaccctctc ctaggactgg         60
attcaacggg gggaggagga tcagcggccg caactgatct tcaccaaacg                   110

<210> SEQ ID NO 22
<211> LENGTH: 106
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (29)..(30)
<223> OTHER INFORMATION: n = a, g, c or t
<220> FEATURE:
<221> NAME/KEY: misc_feature
<222> LOCATION: (32)..(33)
<223> OTHER INFORMATION: n = a, g, c or t
<220> FEATURE:
<221> NAME/KEY: misc_feature
<222> LOCATION: (35)..(36)
<223> OTHER INFORMATION: n = a, g, c or t
<220> FEATURE:
<221> NAME/KEY: misc_feature
<222> LOCATION: (38)..(39)
<223> OTHER INFORMATION: n = a, g, c or t
<220> FEATURE:
<221> NAME/KEY: misc_feature
<222> LOCATION: (41)..(42)
<223> OTHER INFORMATION: n = a, g, c or t
<220> FEATURE:
<221> NAME/KEY: misc_feature
<222> LOCATION: (44)..(45)
<223> OTHER INFORMATION: n = a, g, c or t
<220> FEATURE:
<221> NAME/KEY: misc_feature
<222> LOCATION: (47)..(48)
<223> OTHER INFORMATION: n = a, g, c or t
<220> FEATURE:
<221> NAME/KEY: misc_feature
<222> LOCATION: (50)..(51)
<223> OTHER INFORMATION: n = a, g, c or t
<220> FEATURE:
<221> NAME/KEY: misc_feature
<222> LOCATION: (53)..(54)
<223> OTHER INFORMATION: n = a, g, c or t
<220> FEATURE:
<221> NAME/KEY: misc_feature
<222> LOCATION: (56)..(57)
<223> OTHER INFORMATION: n = a, g, c or t
<220> FEATURE:
<221> NAME/KEY: misc_feature
<222> LOCATION: (59)..(60)
<223> OTHER INFORMATION: n = a, g, c or t

```
<220> FEATURE:
<221> NAME/KEY: misc_feature
<222> LOCATION: (62)..(63)
<223> OTHER INFORMATION: n = a, g, c or t

<400> SEQUENCE: 22
cacacaggaa acaggatcta ccatggccnn bnnbnnbnnb nnbnnbnnbn nbnnbnnbnn     60
bnnbggggga ggaggatcag cggccgcaac tgatcttcac caaacg                  106

<210> SEQ ID NO 23
<211> LENGTH: 20
<212> TYPE: DNA
<213> ORGANISM: Artificial sequence
<220> FEATURE:
<223> OTHER INFORMATION: Primer

<400> SEQUENCE: 23
cagttgatcg gcgcgagatt                                                20

<210> SEQ ID NO 24
<211> LENGTH: 2390
<212> TYPE: DNA
<213> ORGANISM: Artificial sequence
<220> FEATURE:
<223> OTHER INFORMATION: TAC-V5-REPA-CIS-ORI-408 construct

<400> SEQUENCE: 24
cagttgatcg gcgcgagatt taatcgccgc gacaatttgc gacggcgcgt gcagggccag     60
actggaggtg gcaacgccaa tcagcaacga ctgtttgccc gccagttgtt gtgccacgcg    120
gttgggaatg taattcagct ccgccatcgc cgcttccact ttttcccgcg ttttcgcaga    180
aacgtggctg gcctggttca ccacgcggga acggtctga  taagagacac cggcatactc    240
tgcgacatcg tataacgtta ctggtttcac attcaccacc ctgaattgac tctcttccgg    300
gcgctatcat gccataccgc gaaaggtttt gcaccattcg gctagcgatg accctgctga    360
ttggttcgct gaccatttcc ggggtgcgga acggcgttac cagaaactca gaaggttcgt    420
ccaaccaaac cgactctgac ggcagtttac gagagagatg atagggtctg cttcagtaag    480
ccagatgcta cacaattagg cttgtacata ttgtcgttag aacgcggcta caattaatac    540
ataaccttat gtatcataca catacgattt aggtgacact atagaataca agcttactcc    600
ccatccccct gttgacaatt aatcatggct cgtataatgt gtggaattgt gagcggataa    660
caatttcaca caggaaacag gatctaccat ggccggaaaa cctatcccaa ccctctcct    720 aggactggat tcaacggggg gaggaggatc agcggccgca actgatcttc accaaacgta    780
ttaccgccag gtaaagaacc cgaatccggt gtttacaccc cgtgaaggtg caggaacgct    840
gaagttctgc gaaaaactga tggaaaaggc ggtgggcttc acttcccgtt tgatttcgc     900 cattcatgtg gcgcatgccc gttcgcgtgg tctgcgtcga cgcatgccac cagtgctgcg    960
tcgacgggct attgatgcgc tcctgcaggg gctgtgtttc cactatgacc cgctggccaa   1020
ccgcgtccag tgctccatca ccacgctggc cattgagtgc ggactggcga cggagtctgc   1080
tgccggaaaa ctctccatca cccgtgccac ccgggccctg acgttcctgt cagagctggg   1140
actgattacc taccagacgg aatatgaccc gcttatcggg tgctacattc cgaccgatat   1200
cacgttcaca tctgcactgt ttgctgccct cgatgtatca gaggaggcag tggccgccgc   1260
gcgccgcagc cgtgtggtat gggaaaacaa acaacgcaaa aagcaggggc tggataccct   1320
gggcatggat gaactgatag cgaaagcctg cgtttttgtt cgtgagcgtt ttcgcagtta   1380
```

-continued

```
tcagacagag cttaagtccc ggggaataaa gcgtgcccgt gcgcgtcgtg atgcggacag      1440
ggaacgtcag gatattgtca ccctggtgaa acggcagctg acgcgcgaaa tcgcggaagg      1500
gcgcttcact gccaatcgtg aggcggtaaa acgcgaagtt gagcgtcgtg tgaaggagcg      1560
catgattctg tcacgtaacc gtaattacag ccggctggcc acagcttccc cctgaaagtg      1620
acctcctctg aataatccgg cctgcgccgg aggcttccgc acgtctgaag cccgacagcg      1680
cacaaaaaat cagcaccaca tacaaaaaac aacctcatca tccagcttct ggtgcatccg      1740 gcccccctg ttttcgatac aaaacacgcc tcacagacgg ggaattttgc ttatccacat       1800
taaactgcaa gggacttccc cataaggtta caaccgttca tgtcataaag cgccatccgc      1860
cagcgttaca gggtgcaatg tatcttttaa acacctgttt atatctcctt taaactactt      1920
aattacattc atttaaaaag aaaacctatt cactgcctgt cctgtggaca dacagatatg      1980
cacctcccac cgcaagcggc gggcccctac cggagccgct ttagttacaa cactcagaca      2040
caaccaccag aaaaaccccg gtccagcgca gaactgaaac cacaaagccc ctccctcata      2100
actgaaaagc ggccccgccc cggcccgaag ggccggaaca gagtcgcttt taattatgaa      2160
tgttgtaact acttcatcat cgctgtcagt cttctcgctg gaagttctca gtacacgctc      2220
gtaagcggcc ctgacggccc gctaacgcgg agatacgccc cgacttcggg taaaccctcg      2280
tcgggaccac tccgaccgcg cacagaagct ctctcatggc tgaaagcggg tatggtctgg      2340
cagggctggg gatgggtaag gtgaaatcta tcaatcagta ccggcttacg              2390
```

```
<210> SEQ ID NO 25
<211> LENGTH: 2384
<212> TYPE: DNA
<213> ORGANISM: Artificial sequence
<220> FEATURE:
<223> OTHER INFORMATION: TAC-NNB-REPA-CIS-ORI-408 construct
<220> FEATURE:
<221> NAME/KEY: misc_feature
<222> LOCATION: (695)..(696)
<223> OTHER INFORMATION: n = a, g, c or t
<220> FEATURE:
<221> NAME/KEY: misc_feature
<222> LOCATION: (698)..(699)
<223> OTHER INFORMATION: n = a, g, c or t
<220> FEATURE:
<221> NAME/KEY: misc_feature
<222> LOCATION: (701)..(702)
<223> OTHER INFORMATION: n = a, g, c or t
<220> FEATURE:
<221> NAME/KEY: misc_feature
<222> LOCATION: (704)..(705)
<223> OTHER INFORMATION: n = a, g, c or t
<220> FEATURE:
<221> NAME/KEY: misc_feature
<222> LOCATION: (707)..(708)
<223> OTHER INFORMATION: n = a, g, c or t
<220> FEATURE:
<221> NAME/KEY: misc_feature
<222> LOCATION: (710)..(711)
<223> OTHER INFORMATION: n = a, g, c or t
<220> FEATURE:
<221> NAME/KEY: misc_feature
<222> LOCATION: (713)..(714)
<223> OTHER INFORMATION: n = a, g, c or t
<220> FEATURE:
<221> NAME/KEY: misc_feature
<222> LOCATION: (716)..(717)
<223> OTHER INFORMATION: n = a, g, c or t
<220> FEATURE:
<221> NAME/KEY: misc_feature
<222> LOCATION: (719)..(720)
<223> OTHER INFORMATION: n = a, g, c or t
<220> FEATURE:
<221> NAME/KEY: misc_feature
```

```
<222> LOCATION: (722)..(723)
<223> OTHER INFORMATION: n = a, g, c or t
<220> FEATURE:
<221> NAME/KEY: misc_feature
<222> LOCATION: (725)..(726)
<223> OTHER INFORMATION: n = a, g, c or t
<220> FEATURE:
<221> NAME/KEY: misc_feature
<222> LOCATION: (728)..(729)
<223> OTHER INFORMATION: n = a, g, c or t

<400> SEQUENCE: 25
```

| | | | | | |
|---|---|---|---|---|---|
| cagttgatcg | gcgcgagatt | taatcgccgc | gacaatttgc | gacggcgcgt | gcagggccag | 60 |
| actggaggtg | gcaacgccaa | tcagcaacga | ctgtttgccc | gccagttgtt | gtgccacgcg | 120 |
| gttgggaatg | taattcagct | ccgccatcgc | cgcttccact | ttttcccgcg | ttttcgcaga | 180 |
| aacgtggctg | gcctggttca | ccacgcggga | acggtctga | taagagacac | cggcatactc | 240 |
| tgcgacatcg | tataacgtta | ctggtttcac | attcaccacc | ctgaattgac | tctcttccgg | 300 |
| gcgctatcat | gccataccgc | gaaaggtttt | gcaccattcg | gctagcgatg | accctgctga | 360 |
| ttggttcgct | gaccatttcc | ggggtgcgga | acggcgttac | cagaaactca | gaaggttcgt | 420 |
| ccaaccaaac | cgactctgac | ggcagtttac | gagagagatg | atagggtctg | cttcagtaag | 480 |
| ccagatgcta | cacaattagg | cttgtacata | ttgtcgttag | aacgcggcta | caattaatac | 540 |
| ataaccttat | gtatcataca | catacgattt | aggtgacact | atagaataca | agcttactcc | 600 |
| ccatcccct | gttgacaatt | aatcatggct | cgtataatgt | gtggaattgt | gagcggataa | 660 |
| caatttcaca | caggaaacag | gatctaccat | ggccnnbnnb | nnbnnbnnbn | nbnnbnnbnn | 720 |
| bnnbnnbnnb | gggggaggag | gatcagcggc | cgcaactgat | cttcaccaaa | cgtattaccg | 780 |
| ccaggtaaag | aacccgaatc | cggtgtttac | accccgtgaa | ggtgcaggaa | cgctgaagtt | 840 |
| ctgcgaaaaa | ctgatggaaa | aggcggtggg | cttcacttcc | cgttttgatt | tcgccattca | 900 |
| tgtggcgcat | gcccgttcgc | gtggtctgcg | tcgacgcatg | ccaccagtgc | tgcgtcgacg | 960 |
| ggctattgat | gcgctcctgc | aggggctgtg | tttccactat | gacccgctgg | ccaaccgcgt | 1020 |
| ccagtgctcc | atcaccacgc | tggccattga | gtgcggactg | gcgacggagt | ctgctgccgg | 1080 |
| aaaactctcc | atcacccgtg | ccacccgggc | cctgacgttc | ctgtcagagc | tgggactgat | 1140 |
| tacctaccag | acgaatatg | acccgcttat | cgggtgctac | attccgaccg | atatcacgtt | 1200 |
| cacatctgca | ctgtttgctg | ccctcgatgt | atcagaggag | gcagtggccg | ccgcgcgccg | 1260 |
| cagccgtgtg | gtatgggaaa | acaaacaacg | caaaaagcag | gggctggata | ccctgggcat | 1320 |
| ggatgaactg | atagcgaaag | cctggcgttt | tgttcgtgag | cgttttcgca | gttatcagac | 1380 |
| agagcttaag | tcccggggaa | taaagcgtgc | ccgtgcgcgt | cgtgatgcgg | acagggaacg | 1440 |
| tcaggatatt | gtcaccctgg | tgaaacggca | gctgacgcgc | gaaatcgcgg | aagggcgctt | 1500 |
| cactgccaat | cgtgaggcgg | taaaacgcga | agttgagcgt | cgtgtgaagg | agcgcatgat | 1560 |
| tctgtcacgt | aaccgtaatt | acagccggct | ggccacagct | tcccctgaa | agtgacctcc | 1620 |
| tctgaataat | ccggcctgcg | ccggaggctt | ccgcacgtct | gaagcccgac | agcgcacaaa | 1680 |
| aaatcagcac | cacatacaaa | aaacaacctc | atcatccagc | ttctggtgca | tccggcccc | 1740 |
| cctgttttcg | atacaaaaca | cgcctcacag | acggggaatt | ttgcttatcc | acattaaact | 1800 |
| gcaagggact | tccccataag | gttacaaccg | ttcatgtcat | aaagcgccat | ccgccagcgt | 1860 |
| tacagggtgc | aatgtatctt | ttaaacacct | gtttatatct | cctttaaact | acttaattac | 1920 |
| attcatttaa | aaagaaaacc | tattcactgc | ctgtcctgtg | gacagacaga | tatgcacctc | 1980 |

```
ccaccgcaag cggcgggccc ctaccggagc cgctttagtt acaacactca gacacaacca   2040
ccagaaaaac cccggtccag cgcagaactg aaaccacaaa gccctccct cataactgaa    2100 aagcggcccc gccccggccc gaagggccgg aacagagtcg cttttaatta tgaatgttgt   2160
aactacttca tcatcgctgt cagtcttctc gctggaagtt ctcagtacac gctcgtaagc   2220
ggccctgacg gcccgctaac gcggagatac gccccgactt cgggtaaacc ctcgtcggga   2280
ccactccgac cgcgcacaga agctctctca tggctgaaag cgggtatggt ctggcagggc   2340
tggggatggg taaggtgaaa tctatcaatc agtaccggct tacg                    2384
```

```
<210> SEQ ID NO 26
<211> LENGTH: 26
<212> TYPE: DNA
<213> ORGANISM: Artificial sequence
<220> FEATURE:
<223> OTHER INFORMATION: Primer

<400> SEQUENCE: 26
ccccatcccc ctgttgacaa ttaatc                                          26

<210> SEQ ID NO 27
<211> LENGTH: 22
<212> TYPE: DNA
<213> ORGANISM: Artificial sequence
<220> FEATURE:
<223> OTHER INFORMATION: Primer

<400> SEQUENCE: 27
ggtagatcct gtttcctgtg tg                                              22

<210> SEQ ID NO 28
<211> LENGTH: 110
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (37)..(38)
<223> OTHER INFORMATION: n = a, g, c or t
<220> FEATURE:
<221> NAME/KEY: misc_feature
<222> LOCATION: (40)..(41)
<223> OTHER INFORMATION: n = a, g, c or t
<220> FEATURE:
<221> NAME/KEY: misc_feature
<222> LOCATION: (43)..(44)
<223> OTHER INFORMATION: n = a, g, c or t
<220> FEATURE:
<221> NAME/KEY: misc_feature
<222> LOCATION: (46)..(47)
<223> OTHER INFORMATION: n = a, g, c or t
<220> FEATURE:
<221> NAME/KEY: misc_feature
<222> LOCATION: (49)..(50)
<223> OTHER INFORMATION: n = a, g, c or t
<220> FEATURE:
<221> NAME/KEY: misc_feature
<222> LOCATION: (52)..(53)
<223> OTHER INFORMATION: n = a, g, c or t
<220> FEATURE:
<221> NAME/KEY: misc_feature
<222> LOCATION: (55)..(56)
<223> OTHER INFORMATION: n = a, g, c or t
<220> FEATURE:
<221> NAME/KEY: misc_feature
<222> LOCATION: (58)..(59)
<223> OTHER INFORMATION: n = a, g, c or t
<220> FEATURE:
<221> NAME/KEY: misc_feature
```

```
<222> LOCATION: (61)..(62)
<223> OTHER INFORMATION: n = a, g, c or t
<220> FEATURE:
<221> NAME/KEY: misc_feature
<222> LOCATION: (64)..(65)
<223> OTHER INFORMATION: n = a, g, c or t
<220> FEATURE:
<221> NAME/KEY: misc_feature
<222> LOCATION: (67)..(68)
<223> OTHER INFORMATION: n = a, g, c or t
<220> FEATURE:
<221> NAME/KEY: misc_feature
<222> LOCATION: (70)..(71)
<223> OTHER INFORMATION: n = a, g, c or t
<220> FEATURE:
<221> NAME/KEY: misc_feature
<222> LOCATION: (73)..(74)
<223> OTHER INFORMATION: n = a, g, c or t
<220> FEATURE:
<221> NAME/KEY: misc_feature
<222> LOCATION: (76)..(77)
<223> OTHER INFORMATION: n = a, g, c or t
<220> FEATURE:
<221> NAME/KEY: misc_feature
<222> LOCATION: (79)..(80)
<223> OTHER INFORMATION: n = a, g, c or t
<220> FEATURE:
<221> NAME/KEY: misc_feature
<222> LOCATION: (82)..(83)
<223> OTHER INFORMATION: n = a, g, c or t
<220> FEATURE:
<221> NAME/KEY: misc_feature
<222> LOCATION: (85)..(86)
<223> OTHER INFORMATION: n = a, g, c or t
<220> FEATURE:
<221> NAME/KEY: misc_feature
<222> LOCATION: (88)..(89)
<223> OTHER INFORMATION: n = a, g, c or t

<400> SEQUENCE: 28
acataccgtc atgcggccgc tgatcctcct ccccvnnvn nvnnvnnvnn vnnvnnvnnv    60
nnvnnvnnvn nvnnvnnvnn vnnvnnvnng gccatggtag atcctgtttc             110

<210> SEQ ID NO 29
<211> LENGTH: 49
<212> TYPE: DNA
<213> ORGANISM: Artificial sequence
<220> FEATURE:
<223> OTHER INFORMATION: Primer

<400> SEQUENCE: 29
ctggagatgg catcaagggc cccaactgat cttcaccaaa cgtattacc              49

<210> SEQ ID NO 30
<211> LENGTH: 20
<212> TYPE: DNA
<213> ORGANISM: Artificial sequence
<220> FEATURE:
<223> OTHER INFORMATION: Primer

<400> SEQUENCE: 30
ggcgctatca tgccataccg                                              20

<210> SEQ ID NO 31
<211> LENGTH: 20
<212> TYPE: DNA
<213> ORGANISM: Artificial sequence
<220> FEATURE:
<223> OTHER INFORMATION: Primer

<400> SEQUENCE: 31
```

```
accattcggc tagcgatgac                                              20

<210> SEQ ID NO 32
<211> LENGTH: 33
<212> TYPE: DNA
<213> ORGANISM: Artificial sequence
<220> FEATURE:
<223> OTHER INFORMATION: Primer

<400> SEQUENCE: 32
ggtgaagatc agttgcggcc gctgatcctc ctc                               33

<210> SEQ ID NO 33
<211> LENGTH: 22
<212> TYPE: DNA
<213> ORGANISM: Artificial sequence
<220> FEATURE:
<223> OTHER INFORMATION: Primer

<400> SEQUENCE: 33
gattggttcg ctgaccattt cc                                           22

<210> SEQ ID NO 34
<211> LENGTH: 21
<212> TYPE: DNA
<213> ORGANISM: Artificial sequence
<220> FEATURE:
<223> OTHER INFORMATION: Primer

<400> SEQUENCE: 34
cggcgttacc agaaactcag a                                            21

<210> SEQ ID NO 35
<211> LENGTH: 20
<212> TYPE: DNA
<213> ORGANISM: Artificial sequence
<220> FEATURE:
<223> OTHER INFORMATION: Primer

<400> SEQUENCE: 35
aaccgactct gacggcagtt                                              20

<210> SEQ ID NO 36
<211> LENGTH: 18
<212> TYPE: PRT
<213> ORGANISM: Artificial sequence
<220> FEATURE:
<223> OTHER INFORMATION: Peptide

<400> SEQUENCE: 36

Cys Gly Cys Pro Thr Met Ala Ala Arg Val Arg Pro Val Leu Asn Ser
1               5                   10                  15

Lys His

<210> SEQ ID NO 37
<211> LENGTH: 11
<212> TYPE: PRT
<213> ORGANISM: Artificial sequence
<220> FEATURE:
<223> OTHER INFORMATION: Peptide

<400> SEQUENCE: 37

Met Thr Thr Val Pro Val Leu Met Ile Ser Val
1               5                   10
```

```
<210> SEQ ID NO 38
<211> LENGTH: 18
<212> TYPE: PRT
<213> ORGANISM: Artificial sequence
<220> FEATURE:
<223> OTHER INFORMATION: Peptide

<400> SEQUENCE: 38

Thr Leu Ser Thr Arg His His Asn Val Ile Asp Arg Phe Asn Leu Arg
1               5                   10                  15

Asn Phe

<210> SEQ ID NO 39
<211> LENGTH: 18
<212> TYPE: PRT
<213> ORGANISM: Artificial sequence
<220> FEATURE:
<223> OTHER INFORMATION: Peptide

<400> SEQUENCE: 39

Ser Ile Arg Thr Leu Thr Gly Ser Thr Pro Ala Gln Phe Asp Ala Thr
1               5                   10                  15

Ala Asp

<210> SEQ ID NO 40
<211> LENGTH: 12
<212> TYPE: PRT
<213> ORGANISM: Artificial sequence
<220> FEATURE:
<223> OTHER INFORMATION: Peptide

<400> SEQUENCE: 40

Ala Asn Leu Trp Arg Ile Val Leu His Gly Trp Trp
1               5                   10

<210> SEQ ID NO 41
<211> LENGTH: 12
<212> TYPE: PRT
<213> ORGANISM: Artificial sequence
<220> FEATURE:
<223> OTHER INFORMATION: Peptide

<400> SEQUENCE: 41

Val Ser Phe Met Leu Leu Gly Pro His Arg His Arg
1               5                   10

<210> SEQ ID NO 42
<211> LENGTH: 11
<212> TYPE: PRT
<213> ORGANISM: Artificial sequence
<220> FEATURE:
<223> OTHER INFORMATION: Peptide

<400> SEQUENCE: 42

Leu Val Leu His Trp Leu Ser Leu Gly Ser Arg
1               5                   10

<210> SEQ ID NO 43
<211> LENGTH: 12
<212> TYPE: PRT
<213> ORGANISM: Artificial sequence
<220> FEATURE:
<223> OTHER INFORMATION: Peptide

<400> SEQUENCE: 43

Ser Asn Gln Val Val Leu Ile Leu His Leu Arg Pro
```

-continued

```
<210> SEQ ID NO 44
<211> LENGTH: 12
<212> TYPE: PRT
<213> ORGANISM: Artificial sequence
<220> FEATURE:
<223> OTHER INFORMATION: Peptide

<400> SEQUENCE: 44

Ala Glu Ser Trp Leu His Gln Ser Trp Ile His Leu
 1               5                  10

<210> SEQ ID NO 45
<211> LENGTH: 42
<212> TYPE: DNA
<213> ORGANISM: Artificial sequence
<220> FEATURE:
<223> OTHER INFORMATION: Primer

<400> SEQUENCE: 45
caggaaacag gatctaccat gctgcaggag tcaggacctg ag                    42

<210> SEQ ID NO 46
<211> LENGTH: 53
<212> TYPE: DNA
<213> ORGANISM: Artificial sequence
<220> FEATURE:
<223> OTHER INFORMATION: Primer

<400> SEQUENCE: 46
gtttggtgaa gatcagttga tcctcctccc ccccgctcga ggaagatgga tac        53

<210> SEQ ID NO 47
<211> LENGTH: 53
<212> TYPE: DNA
<213> ORGANISM: Artificial sequence
<220> FEATURE:
<223> OTHER INFORMATION: Primer

<400> SEQUENCE: 47
gtatccatct tcctcgagcg gggggagga ggatcaactg atcttcacca aac         53

<210> SEQ ID NO 48
<211> LENGTH: 42
<212> TYPE: DNA
<213> ORGANISM: Artificial sequence
<220> FEATURE:
<223> OTHER INFORMATION: Primer

<400> SEQUENCE: 48
ctcaggtcct gactcctgca gcatggtaga tcctgtttcc tg                    42
```